United States Patent
Liu et al.

(10) Patent No.: US 7,268,126 B2
(45) Date of Patent: Sep. 11, 2007

(54) POLYMORPHIC AND AMORPHOUS FORMS OF THE PHOSPHATE SALT OF 8-FLUORO-2-{4-[(METHYLAMINO)METHYL]PHENYL}-1,3,4,5-TETRAHYDRO-6H-AZEPINO[5,4,3-CE]INDOL-6-ONE

(75) Inventors: Jia Liu, San Diego, CA (US); Naresh Nayyar, San Diego, CA (US); Ming Guo, San Diego, CA (US); Zhen-Ping Wu, La Jolla, CA (US); Bennett Chaplin Borer, San Diego, CA (US); Aparna Nadig Srirangam, San Diego, CA (US); Mark Bryan Mitchell, San Diego, CA (US); Yi Li, San Diego, CA (US); Jan-Jon Chu, Carlsbad, CA (US)

(73) Assignees: Agouron Pharmaceuticals, Inc., San Diego, CA (US); Cancer Research Technology Ltd., London (GB)

( * ) Notice: Subject to any disclaimer, the term of this patent is extended or adjusted under 35 U.S.C. 154(b) by 0 days.

(21) Appl. No.: 11/233,835

(22) Filed: Sep. 21, 2005

(65) Prior Publication Data

US 2006/0100198 A1    May 11, 2006

Related U.S. Application Data

(60) Provisional application No. 60/612,459, filed on Sep. 22, 2004, provisional application No. 60/679,296, filed on May 9, 2005.

(51) Int. Cl.
| | | |
|---|---|---|
| *C07D 487/06* | (2006.01) | |
| *A61K 31/55* | (2006.01) | |
| *A61P 35/00* | (2006.01) | |
| *A61P 35/28* | (2006.01) | |

(52) U.S. Cl. .................................. 514/212.04; 540/520
(58) Field of Classification Search ................ 540/520; 514/212.04
See application file for complete search history.

(56) References Cited

U.S. PATENT DOCUMENTS 6,495,541 B1    12/2002    Webber et al.

FOREIGN PATENT DOCUMENTS

| LB | 6934 | 6/2004 |
| WO | WO 00/42040 | 7/2000 |
| WO | WO 2004/087713 A1 | 10/2004 |

*Primary Examiner*—Bruck Kifle
(74) *Attorney, Agent, or Firm*—Bryan C. Zielinski; Galina M. Yakovleva

(57) ABSTRACT

The present invention relates to novel polymorphic and amorphous forms of a phosphate salt of 8-fluoro-2-{4-[(methylamino)methyl]phenyl}-1,3,4,5-tetrahydro-6H-azepino[5,4,3-cd]indol-6-one, and to processes for their preparation. Such polymorphic forms may be a component of a pharmaceutical composition and may be used to treat a mammalian disease condition mediated by poly(ADP-ribose) polymerase activity including the disease condition such as cancer.

6 Claims, 24 Drawing Sheets

Form V

Form VI

POLYMORPHIC AND AMORPHOUS FORMS OF THE PHOSPHATE SALT OF 8-FLUORO-2-{4-[(METHYLAMINO)METHYL]PHENYL}-1,3,4,5-TETRAHYDRO-6H-AZEPINO[5,4,3-CE]INDOL-6-ONE

This application claims the benefit of U.S. Provisional Application Ser. No. 60/612,459 filed Sep. 22, 2004 and U.S. Provisional Application Ser. No. 60/679,296 filed May 9, 2005, the contents of which are hereby incorporated by reference in their entireties.

FIELD OF THE INVENTION

The present invention relates to novel polymorphic and amorphous forms of the phosphate salt of 8-fluoro-2-{4-[(methylamino)methyl]phenyl}-1,3,4,5-tetrahydro-6H-azepino[5,4,3-cd]indol-6-one, and to methods for their preparation. The invention is also directed to pharmaceutical compositions containing at least one polymorphic or amorphous form and to the therapeutic or prophylactic use of such polymorphic and amorphous forms and compositions.

BACKGROUND OF THE INVENTION

The compound 8-fluoro-2-{4-[(methylamino)methyl]phenyl}-1,3,4,5-tetrahydro-6H-azepino[5,4,3-cd]indol-6-one represented by formula 1

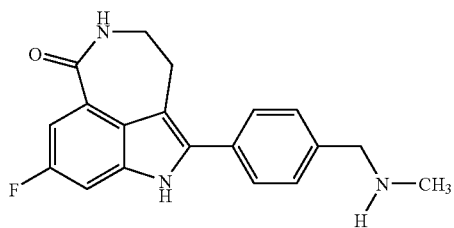

is a small molecule inhibitor of poly(ADP-ribose) polymerase (PARP). The compound of formula 1 and salts thereof, can be prepared as described in U.S. Pat. No. 6,495,541; PCT Application No. PCT/IB2004/000915, International Publication No. WO 2004/087713; and U.S. Provisional Patent Application Ser. No. 60/612,457, the disclosures of which are incorporated herein by reference in their entireties.

To date, eighteen enzymes have been identified by DNA sequence homology in the PARP family and the biochemical and enzymatic properties of seven have been investigated: PARP-1, and PARP-2 are stimulated by DNA strand breaks, PARP-3 interacts with PARP-1 and the centrosome, PARP-4 also known as vault PARP (VPARP), is the largest PARP and is associated with cytoplasmic vaults, tankyrase 1 and 2 (PARP-5a and 5b) are associated with telomeric proteins and the function of PARP-7 (TiPARP) is not clear at present but it may be involved in T-cell function and it can poly(ADP-ribosylate) histones (Ame J C, Splenlehauer C and de Murcia G. The PARP Superfamily. *Bioessays* 26 882-893 (2004)). Pharmacology studies have shown that the compound of formula 1 is an inhibitor of PARP-1 ($K_i$=1.4 nM) and PARP-2 ($K_i$=0.17 nM). Based on structural similarities in the amino acid sequences among the PARP enzymes, the compound of formula 1 likely binds with high affinity to the other members of the family as well.

Enzyme-mediated repair of single- or double-strand breaks in DNA is a potential mechanism of resistance to radiotherapy or cytotoxic drugs whose mechanism depends on DNA damage. Inhibition of DNA repair enzymes is thus a strategy for the potentiation of these agents. PARP-1, the best-characterized member of the PARP family, is a nuclear enzyme that upon activation by DNA damage mediates the transfer of ADP-ribose fragments from $NAD^+$ to a number of acceptor proteins. Depending on the extent of DNA damage incurred, PARP-1 activation and subsequent poly (ADP-ribosyl)ation mediate the repair of the damaged DNA or induce cell death. When DNA damage is moderate, PARP-1 plays a significant role in the DNA repair process. Conversely, in the event of massive DNA damage, excessive activation of PARP-1 depletes ATP pools (in an effort to replenish $NAD^+$), which ultimately leads to cell mortality by necrosis (Tentori L, Portarena I, Graziani G. Potential applications of poly(ADP-ribose) polymerase (PARP) inhibitors. *Pharmacol Res* 2002, 45, 73-85). This activation of PARP can also lead to release of AIF (apoptosis-inducing factor) triggering a caspase-independent apoptotic pathway. (Hong S J, Dawson T M and Dawson V L. Nuclear and mitochondrial conversations in cell death: PARP-1 and AIF. *Trends in Pharmacological Sciences* 25 259-264 (2004)).

As the result of the dual role of PARP-1, inhibitors of this enzyme, such as 8-fluoro-2-{4-[(methylamino)methyl]phenyl}-1,3,4,5-tetrahydro-6H-azepino[5,4,3-cd]indol-6-one represented by formula 1, may have a role as chemosensitizing agents (by preventing DNA repair, for example, after anticancer therapy), or as treatments for a variety of disease and toxic states that involve oxidative or nitric oxide induced stress and subsequent PARP hyperactivation. Such conditions include neurologic and neurodegenerative disorders (e.g., Parkinson's disease, Alzheimer's disease) (Love S, Barber R, Wilcock G K. Increased poly(ADP-ribosyl)ation of nuclear proteins in Alzheimer's disease. Brain 1999;122:247-53; Mandir A S, Przedborski S, Jackson-Lewis V, et al. Poly(ADP-ribose) polymerase activation mediates 1-methyl-4-phenyl-1,2,3,6-tetrahydropyridine (MPTP)-induced parkinsonism. Proc Natl Acad Sci USA 1999;96:5774-9); cardiovascular disorders (e.g., myocardial infarction, ischemia-reperfusion injury) (Pieper A A, Walles T, Wei G, et al. Myocardial postischemic injury is reduced by poly(ADP-ribose) polymerase-1 gene disruption. J Mol Med 2000;6:271-82; Szabó G, Bährle S, Stumpf N, et al. Poly(ADP-ribose) polymerase inhibition reduces reperfusion injury after heart transplantation. Circ Res 2002;90: 100-6; U.S. Pat. No. 6,423,705); inflammatory diseases, (Szabó C, Dawson V. Role of poly(ADP-ribose) synthetase in inflammation and ischaemia-reperfusion. TIPS 1998;19: 287-98); diabetic vascular dysfunction (Soriano F G, Virág L, Szabó C. Diabetic endothelial dysfunction: role of reactive oxygen and nitrogen species production and poly(ADP-ribose) polymerase activation. J Mol Med 2001;79:437-48); arthritis (Szabó C, Virág L, Cuzzocrea S, et al. Protection against peroxynitrite-induced fibroblast injury and arthritis development by inhibition of poly(ADP-ribose) synthase. Proc Natl Acad Sci USA 1998;95:3867-72); and cisplatin-induced nephrotoxicity (Racz I, Tory K, Gallyas F, et al. BGP-15—a novel poly(ADP-ribose) polymerase inhibitor—protects against nephrotoxicity of cisplatin without compromising its antitumor activity. Biochem Pharmacol 2002;63:1099-111). Furthermore, it was shown that BRCA2 deficient tumor cells are acutely sensitive to PARP-1 inhibitors alone (Bryant H E, Schultz N, Thomas H D, Parker K M, Flower D, Lopez E, Kyle S, Meuth M, Curtin N J and Helleday T. "Specific killing of BRCA2 deficient tumors with inhibitors of poly(ADP-ribose)polymerase," *Nature*: in press). PARP inhibitors are also involved in enhancing the induction of the expression of Reg gene in β cells and HGF gene and, accordingly, promote the proliferation of pancreatic β-cells of Langerhans' islets and suppress apoptosis of the cells (U.S. Patent Application Publication 2004/0091453; PCT Publication No. WO 02/00665). In addition, PARP inhibitors are also used in cosmetic preparations, especially in after-sun lotions (PCT Publication No. WO 01/82877). There are no marketed PARP inhibitors presently.

Cancer remains a disease with high unmet medical need. Cytotoxic chemotherapy remains the mainstay of systemic therapy for the majority of cancers, particularly late-stage disease. However, for patients with advanced or metastatic disease, few of the cytotoxic chemotherapy agents or regimens have been effective in increasing overall survival. Furthermore, the small therapeutic window associated with cytotoxic agents results in significant toxicity in conjunction with suboptimal efficacy. Therefore, a chemosensitizer that enhances the efficacy of cytotoxic drugs at well-tolerated doses would fulfill a critical need for cancer patients. U.S. Provisional Patent Applications No. 60/612,458 and 60/683,006, entitled "Therapeutic Combinations Comprising Poly (ADP-Ribose) Polymerases Inhibitor," the disclosures of which are incorporated herein by reference in its entirety, describe pharmaceutical combinations of 8-fluoro-2-{4-[(methylamino)methyl]phenyl}-1,3,4,5-tetrahydro-6H-azepino[5,4,3-cd]indol-6-one.

To prepare pharmaceutical compositions containing 8-fluoro-2-{4-[(methylamino)methyl]phenyl}-1,3,4,5-tetrahydro-6H-azepino[5,4,3-cd]indol-6-one for administration to mammals, there is a need to produce this compound in a form having physical properties amenable to reliable formulation. Accordingly, there is a need in the art to provide improved forms of 8-fluoro-2-{4-[(methylamino)methyl] phenyl}-1,3,4,5-tetrahydro-6H-azepino[5,4,3-cd]indol-6-one having enhanced properties, such as improved solubility or bioavailability and stability to heat, moisture, and light.

SUMMARY OF THE INVENTION

In one aspect, the present invention provides six polymorphic forms and one amorphous form of the phosphate salt of 8-fluoro-2-{4-[(methylamino)methyl]phenyl}1,3,4,5-tetrahydro-6H-azepino[5,4,3-cd]indol-6-one.

In one embodiment, the present invention provides a crystalline phosphate salt of 8-fluoro-2-{4-[(methylamino) methyl]phenyl}1,3,4,5-tetrahydro-6H-azepino[5,4,3-cd]indol-6-one, wherein the salt is a substantially pure polymorph of Form I.

In another embodiment, the invention provides a crystalline phosphate salt of 8-fluoro-2-{4-[(methylamino)methyl] phenyl}1,3,4,5-tetrahydro-6H-azepino[5,4,3-cd]indol-6-one, wherein the salt is a substantially pure polymorph of Form II.

In another embodiment, the invention provides a crystalline phosphate salt of 8-fluoro-2-{4-[(methylamino)methyl] phenyl}1,3,4,5-tetrahydro-6H-azepino[5,4,3-cd]indol-6-one, wherein the salt is a substantially pure polymorph of Form III.

In another embodiment, the invention provides a crystalline phosphate salt of 8-fluoro-2-{4-[(methylamino)methyl] phenyl}1,3,4,5-tetrahydro-6H-azepino[5,4,3-cd]indol-6-one, wherein the salt is a substantially pure polymorph of Form IV.

In another embodiment, the invention provides a crystalline phosphate salt of 8-fluoro-2-{4-[(methylamino)methyl] phenyl}1,3,4,5-tetrahydro-6H-azepino[5,4,3-cd]indol-6-one, wherein the salt is a substantially pure polymorph of Form V.

In another embodiment, the invention provides a crystalline phosphate salt of 8-fluoro-2-{4-[(methylamino)methyl] phenyl}1,3,4,5-tetrahydro-6H-azepino[5,4,3-cd]indol-6-one, wherein the salt is a substantially pure polymorph of Form VI.

In another embodiment, the invention provides a phosphate salt of 8-fluoro-2-{4-[(methylamino)methyl]phenyl}1,3,4,5-tetrahydro-6H-azepino[5,4,3-cd]indol-6-one, wherein the salt is a substantially pure amorphous form.

In another embodiment, the invention provides a crystalline phosphate salt of 8-fluoro-2-{4-[(methylamino)methyl] phenyl}1,3,4,5-tetrahydro-6H-azepino[5,4,3-cd]indol-6-one, wherein the salt is a substantially pure polymorph of Form I, having a X-ray powder diffraction pattern comprising peaks at diffraction angles (2θ) of 10.9, 19.3, 22.9, and 25.0.

In another embodiment, the invention provides a crystalline phosphate salt of 8-fluoro-2-{4-[(methylamino)methyl] phenyl}1,3,4,5-tetrahydro-6H-azepino[5,4,3-cd]indol-6-one, wherein the salt is a substantially pure polymorph of Form II, having a X-ray powder diffraction pattern comprising peaks at diffraction angles (2θ) of 11.2, 14.0, 20.1, and 23.1.

In another embodiment, the invention provides a crystalline phosphate salt of 8-fluoro-2-{4-[(methylamino)methyl] phenyl}1,3,4,5-tetrahydro-6H-azepino[5,4,3-cd]indol-6-one, wherein the salt is a substantially pure polymorph of Form III, having a X-ray powder diffraction pattern comprising peaks at diffraction angles (2θ) of 10.7, 11.0, 19.4, and 25.1.

In another embodiment, the invention provides a crystalline phosphate salt of 8-fluoro-2-{4-[(methylamino)methyl] phenyl}1,3,4,5-tetrahydro-6H-azepino[5,4,3-cd]indol-6-one, wherein the salt is a substantially pure polymorph of Form IV, having an X-ray powder diffraction pattern comprising peaks at diffraction angles (2θ) of 8.2, 16.5, 23.0, and 24.8.

In another embodiment, the invention provides a crystalline phosphate salt of 8-fluoro-2-{4-[(methylamino)methyl] phenyl}1,3,4,5-tetrahydro-6H-azepino[5,4,3-cd]indol-6-one, wherein the salt is a substantially pure polymorph of Form V, having an X-ray powder diffraction pattern comprising peaks at diffraction angles (2θ) of 10.8, 14.8, 21.6, and 25.8.

In another embodiment, the invention provides a crystalline phosphate salt of 8-fluoro-2-{4-[(methylamino)methyl] phenyl}1,3,4,5-tetrahydro-6H-azepino[5,4,3-cd]indol-6-one, wherein the salt is a substantially pure polymorph of Form VI, having an X-ray powder diffraction pattern comprising peaks at diffraction angles (2θ) of 14.8, 20.0, 22.3, and 23.5.

In another embodiment, the invention provides a crystalline phosphate salt of 8-fluoro-2-{4-[(methylamino)methyl] phenyl}1,3,4,5-tetrahydro-6H-azepino[5,4,3-cd]indol-6-one, wherein the salt is a substantially pure polymorph of Form I, having an X-ray powder diffraction pattern comprising peaks at diffraction angles (2θ) essentially the same as shown in FIG. 1.

In another embodiment, the invention provides a crystalline phosphate salt of 8-fluoro-2-{4-[(methylamino)methyl] phenyl}1,3,4,5-tetrahydro-6H-azepino[5,4,3-cd]indol-6-one, wherein the salt is a substantially pure polymorph of Form II, having an X-ray powder diffraction pattern comprising peaks at diffraction angles (2θ) essentially the same as shown in FIG. 4.

In another embodiment, the invention provides a crystalline phosphate salt of 8-fluoro-2-{4-[(methylamino)methyl]phenyl}1,3,4,5-tetrahydro-6H-azepino[5,4,3-cd]indol-6-one, wherein the salt is a substantially pure polymorph of Form III, having an X-ray powder diffraction pattern comprising peaks at diffraction angles (2θ) essentially the same as shown in FIG. 7.

In another embodiment, the invention provides a crystalline phosphate salt of 8-fluoro-2-{4-[(methylamino)methyl]phenyl}1,3,4,5-tetrahydro-6H-azepino[5,4,3-cd]indol-6-one, wherein the salt is a substantially pure polymorph of Form IV, having an X-ray powder diffraction pattern comprising peaks at diffraction angles (2θ) essentially the same as shown in FIG. 10.

In another embodiment, the invention provides a crystalline phosphate salt of 8-fluoro-2-{4-[(methylamino)methyl]phenyl}1,3,4,5-tetrahydro-6H-azepino[5,4,3-cd]indol-6-one, wherein the salt is a substantially pure polymorph of Form V, having an X-ray powder diffraction pattern comprising peaks at diffraction angles (2θ) essentially the same as shown in FIG. 13.

In another embodiment, the invention provides a crystalline phosphate salt of 8-fluoro-2-{4-[(methylamino)methyl]phenyl}1,3,4,5-tetrahydro-6H-azepino[5,4,3-cd]indol-6-one, wherein the salt is a substantially pure polymorph of Form VI, having an X-ray powder diffraction pattern comprising peaks at diffraction angles (2θ) essentially the same as shown in FIG. 18.

In another embodiment, the invention provides an amorphous form of the phosphate salt of 8-fluoro-2-{4-[(methylamino)methyl]phenyl}1,3,4,5-tetrahydro-6H-azepino[5,4,3-cd]indol-6-one, where the amorphous form has an X-ray powder diffraction pattern exhibiting a broad peak at diffraction angles (2θ) ranging from 4 to 40° without any of the sharp peaks characteristic of a crystalline form. More particularly, the amorphous form is characterized by having an X-ray powder diffraction pattern essentially the same as shown in FIG. 21. Even more particularly, the amorphous form is characterized by a Raman spectra comprising shift peaks (cm$^{-1}$) essentially the same as shown in FIG. 23.

In another embodiment, the invention provides a solid form of a phosphate salt of 8-fluoro-2-{4-[(methylamino)methyl]phenyl}-1,3,4,5-tetrahydro-6H-azepino[5,4,3-cd]indol-6-one, wherein the solid form comprises at least two of the following forms: polymorph Forms I, II, III, IV, V, VI, and an amorphous form.

In another embodiment, the invention provides a pharmaceutical composition comprising a crystalline phosphate salt of 8-fluoro-2-{4-[(methylamino)methyl]phenyl}1,3,4,5-tetrahydro-6H-azepino[5,4,3-cd]indol-6-one, wherein the salt is a substantially pure polymorph of Form I.

In another embodiment, the invention provides a pharmaceutical composition comprising a crystalline phosphate salt of 8-fluoro-2-{4-[(methylamino)methyl]phenyl}1,3,4,5-tetrahydro-6H-azepino[5,4,3-cd]indol-6-one, wherein the salt is a substantially pure polymorph of Form II.

In another embodiment, the invention provides a pharmaceutical composition comprising a crystalline phosphate salt of 8-fluoro-2-{4-[(methylamino)methyl]phenyl}1,3,4,5-tetrahydro-6H-azepino[5,4,3-cd]indol-6-one, wherein the salt is a substantially pure polymorph of Form III.

In another embodiment, the invention provides a pharmaceutical composition comprising a crystalline phosphate salt of 8-fluoro-2-{4-[(methylamino)methyl]phenyl}1,3,4,5-tetrahydro-6H-azepino[5,4,3-cd]indol-6-one, wherein the salt is a substantially pure polymorph of Form IV.

In another embodiment, the invention provides a pharmaceutical composition comprising a crystalline phosphate salt of 8-fluoro-2-{4-[(methylamino)methyl]phenyl}1,3,4,5-tetrahydro-6H-azepino[5,4,3-cd]indol-6-one, wherein the salt is a substantially pure polymorph of Form V.

In another embodiment, the invention provides a pharmaceutical composition comprising a crystalline phosphate salt of 8-fluoro-2-{4-[(methylamino)methyl]phenyl}1,3,4,5-tetrahydro-6H-azepino[5,4,3-cd]indol-6-one, wherein the salt is a substantially pure polymorph of Form VI.

In another embodiment, the invention provides a pharmaceutical composition comprising a phosphate salt of 8-fluoro-2-{4-[(methylamino)methyl]phenyl}1,3,4,5-tetrahydro-6H-azepino[5,4,3-cd]indol-6-one, wherein the salt is a substantially pure amorphous form.

In another embodiment, the invention provides a pharmaceutical composition comprising a solid form of a phosphate salt of 8-fluoro-2-{4-[(methylamino)methyl]phenyl}-1,3,4,5-tetrahydro-6H-azepino[5,4,3-cd]indol-6-one, wherein the solid form comprises at least two of the following forms: polymorph Forms I, II, III, IV, V, VI, or an amorphous form.

In another embodiment, the invention provides a method of treating a mammalian disease condition mediated by poly(ADP-ribose) polymerase activity, the method comprising administering to a mammal in need thereof a therapeutically effective amount of a pharmaceutical composition comprising a crystalline phosphate salt of 8-fluoroof 8-fluoro-2-{4-[(methylamino)methyl]phenyl}1,3,4,5-tetrahydro-6H-azepino[5,4,3-cd]indol-6-one, wherein the salt is a substantially pure polymorph of Form II.

In another embodiment, the invention provides a method of treating a mammalian disease condition mediated by poly(ADP-ribose) polymerase activity, the method comprising administering to a mammal in need thereof a therapeutically effective amount of a pharmaceutical composition comprising a crystalline phosphate salt of 8-fluoro-2-{4-[(methylamino)methyl]phenyl}1,3,4,5-tetrahydro-6H-azepino[5,4,3-cd]indol-6-one, wherein the salt is a substantially pure polymorph of Form II.

In another embodiment, the invention provides a method of treating a mammalian disease condition mediated by poly(ADP-ribose) polymerase activity, the method comprising administering to a mammal in need thereof a therapeutically effective amount of a pharmaceutical composition comprising a crystalline phosphate salt of 8-fluoro-2-{4-[(methylamino)methyl]phenyl}1,3,4,5-tetrahydro-6H-azepino[5,4,3-cd]indol-6-one, wherein the salt is a substantially pure polymorph of Form III.

In another embodiment, the invention provides a method of treating a mammalian disease condition mediated by poly(ADP-ribose) polymerase activity, the method comprising administering to a mammal in need thereof a therapeutically effective amount of a pharmaceutical composition comprising a crystalline phosphate salt of 8-fluoro-2-{4-[(methylamino)methyl]phenyl}1,3,4,5-tetrahydro-6H-azepino[5,4,3-cd]indol-6-one, wherein the salt is a substantially pure polymorph of Form IV.

In another embodiment, the invention provides a method of treating a mammalian disease condition mediated by poly(ADP-ribose) polymerase activity, the method comprising administering to a mammal in need thereof a therapeutically effective amount of a pharmaceutical composition comprising a crystalline phosphate salt of 8-fluoro-2-{4-

[(methylamino)methyl]phenyl}1,3,4,5-tetrahydro-6H-azepino[5,4,3-cd]indol-6-one, wherein the salt is a substantially pure polymorph of Form V.

In another embodiment, the invention provides a method of treating a mammalian disease condition mediated by poly(ADP-ribose) polymerase activity, the method comprising administering to a mammal in need thereof a therapeutically effective amount of a pharmaceutical composition comprising a crystalline phosphate salt of 8-fluoro-2-{4-[(methylamino)methyl]phenyl}1,3,4,5-tetrahydro-6H-azepino[5,4,3-cd]indol-6-one, wherein the salt is a substantially pure polymorph of Form VI.

In another embodiment, the invention provides a method of treating a mammalian disease condition mediated by poly(ADP-ribose) polymerase activity, the method comprising administering to a mammal in need thereof a therapeutically effective amount of a pharmaceutical composition comprising a phosphate salt of 8-fluoro-2-{4-[(methylamino)methyl]phenyl}1,3,4,5-tetrahydro-6H-azepino[5,4,3-cd]indol-6-one, wherein the salt is a substantially pure amorphous form.

In another embodiment, the invention provides a method of treating a mammalian disease condition mediated by poly(ADP-ribose) polymerase activity, the method comprising administering to a mammal in need thereof a therapeutically effective amount of a pharmaceutical composition comprising a solid form of a phosphate salt of 8-fluoro-2-{4-[(methylamino)methyl]phenyl}-1,3,4,5-tetrahydro-6H-azepino[5,4,3-cd]indol-6-one, wherein the solid form comprises at least two of the following forms: polymorph Forms I, II, III, IV, V, VI, and an amorphous form.

In another embodiment, the invention provides a method of treating cancer in a mammal, the method comprising administering to the mammal a therapeutically effective amount of a pharmaceutical composition comprising a crystalline phosphate salt of 8-fluoro-2-{4-[(methylamino)methyl]phenyl}1,3,4,5-tetrahydro-6H-azepino[5,4,3-cd]indol-6-one, wherein the salt is a substantially pure polymorph of Form I.

In another embodiment, the invention provides a method of treating cancer in a mammal, the method comprising administering to the mammal a therapeutically effective amount of a pharmaceutical composition comprising a crystalline phosphate salt of 8-fluoro-2-{4-[(methylamino)methyl]phenyl}1,3,4,5-tetrahydro-6H-azepino[5,4,3-cd]indol-6-one, wherein the salt is a substantially pure polymorph of Form II.

In another embodiment, the invention provides a method of treating cancer in a mammal, the method comprising administering to the mammal a therapeutically effective amount of a pharmaceutical composition comprising a crystalline phosphate salt of 8-fluoro-2-{4-[(methylamino)methyl]phenyl}1,3,4,5-tetrahydro-6H-azepino[5,4,3-cd]indol-6-one, wherein the salt is a substantially pure polymorph of Form III.

In another embodiment, the invention provides a method of treating cancer in a mammal, the method comprising administering to the mammal a therapeutically effective amount of a pharmaceutical composition comprising a crystalline phosphate salt of 8-fluoro-2-{4-[(methylamino)methyl]phenyl}1,3,4,5-tetrahydro-6H-azepino[5,4,3-cd]indol-6-one, wherein the salt is a substantially pure polymorph of Form IV.

In another embodiment, the invention provides a method of treating cancer in a mammal, the method comprising administering to the mammal a therapeutically effective amount of a pharmaceutical composition comprising a crystalline phosphate salt of 8-fluoro-2-{4-[(methylamino)methyl]phenyl}1,3,4,5-tetrahydro-6H-azepino[5,4,3-cd]indol-6-one, wherein the salt is a substantially pure polymorph of Form V.

In another embodiment, the invention provides a method of treating cancer in a mammal, the method comprising administering to the mammal a therapeutically effective amount of a pharmaceutical composition comprising a crystalline phosphate salt of 8-fluoro-2-{4-[(methylamino)methyl]phenyl}1,3,4,5-tetrahydro-6H-azepino[5,4,3-cd]indol-6-one, wherein the salt is a substantially pure polymorph of Form VI.

In another embodiment, the invention provides a method of treating cancer in a mammal, the method comprising administering to the mammal a therapeutically effective amount of a pharmaceutical composition comprising a phosphate salt of 8-fluoro-2-{4-[(methylamino)methyl]phenyl}1,3,4,5-tetrahydro-6H-azepino[5,4,3-cd]indol-6-one, wherein the salt is a substantially pure amorphous form.

In another embodiment, the invention provides a method of treating cancer in a mammal, the method comprising administering to a mammal in need thereof a therapeutically effective amount of a pharmaceutical composition comprising a solid form of a phosphate salt of 8-fluoro-2-{4-[(methylamino)methyl]phenyl}-1,3,4,5-tetrahydro-6H-azepino[5,4,3-cd]indol-6-one, wherein the solid form comprises at least two of the following forms: polymorph Forms I, II, III, IV, V, VI, or an amorphous form.

In another embodiment, the invention provides a dosage form comprising 8-fluoro-2-{4-[(methylamino)methyl]phenyl}1,3,4,5-tetrahydro-6H-azepino[5,4,3-cd]indol-6-one, wherein the dosage form is a lyophilized powder for injection, which dosage form, upon reconstitution with sterile water for injection, provides a final concentration of 8-fluoro-2-{4-[(methylamino)methyl]phenyl}1,3,4,5-tetrahydro-6H-azepino[5,4,3-cd]indol-6-one as a free base from 1.0 to 4.5 mg/mL at pH from 8.0 to 3.0.

In another embodiment, the invention provides a dosage form comprising 8-fluoro-2-{4-[(methylamino)methyl]phenyl}1,3,4,5-tetrahydro-6H-azepino[5,4,3-cd]indol-6-one, wherein the dosage form is a lyophilized powder for injection, which dosage form, upon reconstitution with sterile water for injection, provides a final concentration of 8-fluoro-2-{4-[(methylamino)methyl]phenyl}1,3,4,5-tetrahydro-6H-azepino[5,4,3-cd]indol-6-one as a free base from 2 to 3 mg/mL at pH from 5.0 to 6.0.

Definitions

The term "Compound I" refers to the phosphate salt of 8-fluoro-2-{4-[(methylamino)methyl]phenyl}-1,3,4,5-tetrahydro-6H-azepino[5,4,3-cd]indol-6-one. The term "the compound of formula 1" refers to 8-fluoro-2-{4-[(methylamino)methyl]phenyl}-1,3,4,5-tetrahydro-6H-azepino[5,4,3-cd]indol-6-one, free base.

The term "active agent" or "active ingredient" refers to a polymorphic form of the phosphate salt of 8-fluoro-2-{4-[(methylamino)methyl]phenyl}-1,3,4,5-tetrahydro-6H-azepino[5,4,3-cd]indol-6-one ("Compound I"), or to a solid form that comprises two or more polymorphic forms or amorphous form of the phosphate salt of 8-fluoro-2-{4-[(methylamino)methyl]phenyl}-1,3,4,5-tetrahydro-6H-azepino[5,4,3-cd]indol-6-one (Compound I).

The term "ambient temperature" refers to a temperature condition typically encountered in a laboratory setting. This includes the approximate temperature range of about 20 to about 30° C.

The term "amorphous" refers to a non-crystalline form of a compound.

The term "aqueous base" refers to any organic or inorganic base. Aqueous bases include, by way of example only, metal bicarbonates, such as sodium bicarbonate, potassium carbonate, cesium carbonate, and the like.

The term "aromatic solvent" refers to an organic solvent possessing an aromatic moiety, including by way of example only, benzene, toluene, xylene isomers or mixtures thereof, and the like.

The term "chemical stability" refers to a type of stability in which a particular compound maintains its chemical integrity, and includes, but is not limited to, thermal stability, light stability, and moisture stability.

The term "detectable amount" refers to an amount or amount per unit volume that can be detected using conventional techniques, such as X-ray powder diffraction, differential scanning calorimetry, HPLC, Fourier Transform Infrared Spectroscopy (FT-IR), Raman spectroscopy, and the like.

The term "exposing to humidity" refers to the process of exposing a substance to water vapor in a humidor, humidity chamber, or any apparatus capable of controlling relative humidity. The term may also describe the process of exposing a substance to ambient humidity as during storage.

The term "cancer" includes, but is not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said method, said abnormal cell growth is a benign proliferative disease, including, but not limited to, psoriasis, benign prostatic hypertrophy or restinosis.

The term "inert solvent" refers to any solvent or liquid component of a slurry that does not chemically react with other components in a solution or slurry. Inert solvents include, by way of example only aprotic solvents such as aromatic solvents, ethyl acetate, acetone, methyl tert-butylether, dioxane, terahydrofuran (THF), and the like. Protic solvents include, by way of example only, methanol, ethanol, propanol isomers, butanol isomers and the like.

The term "mediated by poly(ADP-ribose) polymerase (PARP) activity" refers to biological or molecular processes that are regulated, modulated, or inhibited by PARP activity. For certain applications, inhibition of the PARP activity associated with cancer is preferred. The present invention includes methods of modulating or inhibiting PARP activity, for example in mammals, by administering polymorphic forms of the phosphate salt of 8-fluoro-2-{4-[(methylamino) methyl]phenyl}-1,3,4,5-tetrahydro-6H-azepino[5,4,3-cd]indol-6-one (Compound I), or a solid form that comprises two or more polymorphic forms of Compound I. The activity or efficacy of polymorphs of Compound I, or a solid form that comprises two or more polymorphic forms of Compound I may be measured as described, for example, in U.S. Pat. No. 6,495,541 and U.S. Provisional Patent Application No. 60/612,458, the disclosure of which is incorporated herein by reference in its entirety.

The term "minimal amount" refers to the least amount of solvent required to completely dissolve a substance at a given temperature.

As used herein, the term "polymorph" refers to different crystalline forms of the same compound and other solid state molecular forms including pseudo-polymorphs, such as hydrates (e.g., bound water present in the crystalline structure) and solvates (e.g., bound solvents other than water) of the same compound. Different crystalline polymorphs have different crystal structures due to a different packing of the molecules in the lattice. This results in a different crystal symmetry and/or unit cell parameters which directly influences its physical properties such the X-ray diffraction characteristics of crystals or powders. A different polymorph, for example, will in general diffract at a different set of angles and will give different values for the intensities. Therefore X-ray powder diffraction can be used to identify different polymorphs, or a solid form that comprises more than one polymorph, in a reproducible and reliable way (S. Byrn et al, Pharmaceutical Solids: A Strategic Approach to Regulatory Considerations, Pharmaceutical research, Vol. 12, No. 7, p. 945-954, 1995; J. K. Haleblian and W. McCrone, Pharmacetical Applications of Polymorphism, Journal of Pharmaceutical Sciences, Vol. 58, No. 8, p. 911-929, 1969). Crystalline polymorphic forms are of interest to the pharmaceutical industry and especially to those involved in the development of suitable dosage forms. If the polymorphic form is not held constant during clinical or stability studies, the exact dosage form used or studied may not be comparable from one lot to another. It is also desirable to have processes for producing a compound with the selected polymorphic form in high purity when the compound is used in clinical studies or commercial products since impurities present may produce undesired toxicological effects. Certain polymorphic forms may exhibit enhanced thermodynamic stability or may be more readily manufactured in high purity in large quantities, and thus are more suitable for inclusion in pharmaceutical formulations. Certain polymorphs may display other advantageous physical properties such as lack of hygroscopic tendencies, improved solubility, and enhanced rates of dissolution due to different lattice energies.

The term "peak intensities" refers to relative signal intensities within a given X-ray diffraction pattern. Factors which can affect the relative peak intensities are sample thickness and preferred orientation (i.e., the crystalline particles are not distributed randomly).

The term "peak positions" as used herein refers to X-ray reflection positions as measured and observed in X-ray powder diffraction experiments. Peak positions are directly related to the dimensions of the unit cell. The peaks, identified by their respective peak positions, have been extracted from the diffraction patterns for the various polymorphic Forms I, II, III, IV, V, and VI of the phosphate salt of 8-fluoro-2-{4-[(methylamino)methyl]phenyl}-1,3,4,5-tetrahydro-6H-azepino[5,4,3-cd]indol-6-one (Compound I).

The term "PEG" refers to poly(ethylene glycol). PEG is commercially available having different ranges of polymer chain lengths and thus viscosities. PEG 400 is soluble in alcohols, acetone, benzene, chloroform, acetic acid, $CCl_4$, and water.

The term "pharmaceutically acceptable, carrier, diluent, or vehicle" refers to a material (or materials) that may be included with a particular pharmaceutical agent to form a pharmaceutical composition, and may be solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like.

The term "pharmaceutical composition" refers to a mixture of one or more of the compounds or polymorphs described herein, or physiologically/pharmaceutically acceptable salts or solvates thereof, with other chemical components, such as physiologically/pharmaceutically acceptable carriers and excipients. The purpose of a pharmaceutical composition is to facilitate administration of a compound to an organism.

The term "recrystallize" refers to the process of completely dissolving a solid in a first solvent with heating if necessary, and then inducing precipitation, usually by cooling the solution, or by adding a second solvent in which the solid is poorly soluble.

The term "relative humidity" refers to the ratio of the amount of water vapor in air at a given temperature to the maximum amount of water vapor that can be held at that temperature and pressure, expressed as a percentage.

The term "relative intensity" refers to an intensity value derived from a sample X-ray diffraction pattern. The complete ordinate range scale for a diffraction pattern is assigned a value of 100. A peak having intensity falling between about 50% to about 100% on this scale intensity is termed very strong (vs); a peak having intensity falling between about 50% to about 25% is termed strong (s). Additional weaker peaks are present in typical diffraction patterns and are also characteristic of a given polymorph.

The term "slurry" refers to a solid substance suspended in a liquid medium, typically water or an organic solvent.

The term "separating from" refers to a step in a synthesis in which the desired agent is isolated from other non-desired agents, including, but not limited to any of the following steps: filtering, washing with extra solvent or water, drying with heat and or under vacuum.

The term "substantially pure" with reference to particular polymorphic forms of the phosphate salt of 8-fluoro-2-{4-[(methylamino)methyl]phenyl}-1,3,4,5-tetrahydro-6H-azepino[5,4,3-cd]indol-6-one (Compound I) means the polymorphic form includes less than 10%, preferably less than 5%, preferably less than 3%, preferably less than 1% by weight of impurities, including other polymorphic forms of Compound I. Such purity may be determined, for example, by X-ray powder diffraction.

An "effective amount" is intended to mean that amount of an agent that significantly inhibits proliferation and/or prevents de-differentiation of a eukaryotic cell, e.g., a mammalian, insect, plant or fungal cell, and is effective for the indicated utility, e.g., specific therapeutic treatment.

The term "therapeutically effective amount" refers to that amount of the compound or polymorph being administered which will relieve to some extent one or more of the symptoms of the disorder being treated. In reference to the treatment of cancer, a therapeutically effective amount refers to that amount which has at least one of the following effects:

(1) reducing the size of the tumor;
(2) inhibiting (that is, slowing to some extent, preferably stopping) tumor metastasis;
(3) inhibiting to some extent (that is, slowing to some extent, preferably stopping) tumor growth, and
(4) relieving to some extent (or, preferably, eliminating) one or more symptoms associated with the cancer.

The term "2 theta value" or "2θ" refers to the peak position based on the experimental setup of the X-ray diffraction experiment and is a common abscissa unit in diffraction patterns. The experimental setup requires that if a reflection is diffracted when the incoming beam forms an angle theta (θ) with a certain lattice plane, the reflected beam is recorded at an angle 2 theta (2θ).

The terms "treat", "treating" and "treatment" refer to a method of alleviating or abrogating a hyperproliferative disorder and/or its attendant symptoms. With regard particularly to cancer, these terms simply mean that the life expectancy of an individual affected with a cancer will be increased or that one or more of the symptoms of the disease will be reduced.

The term "under vacuum" refers to typical pressures obtainable by a laboratory oil or oil-free diaphragm vacuum pump.

The term "X-ray powder diffraction pattern" refers to the experimentally observed diffractogram or parameters derived therefrom. X-Ray powder diffraction patterns are characterized by peak position (abscissa) and peak intensities (ordinate).

DETAILED DESCRIPTION OF THE INVENTION

Figure 1:
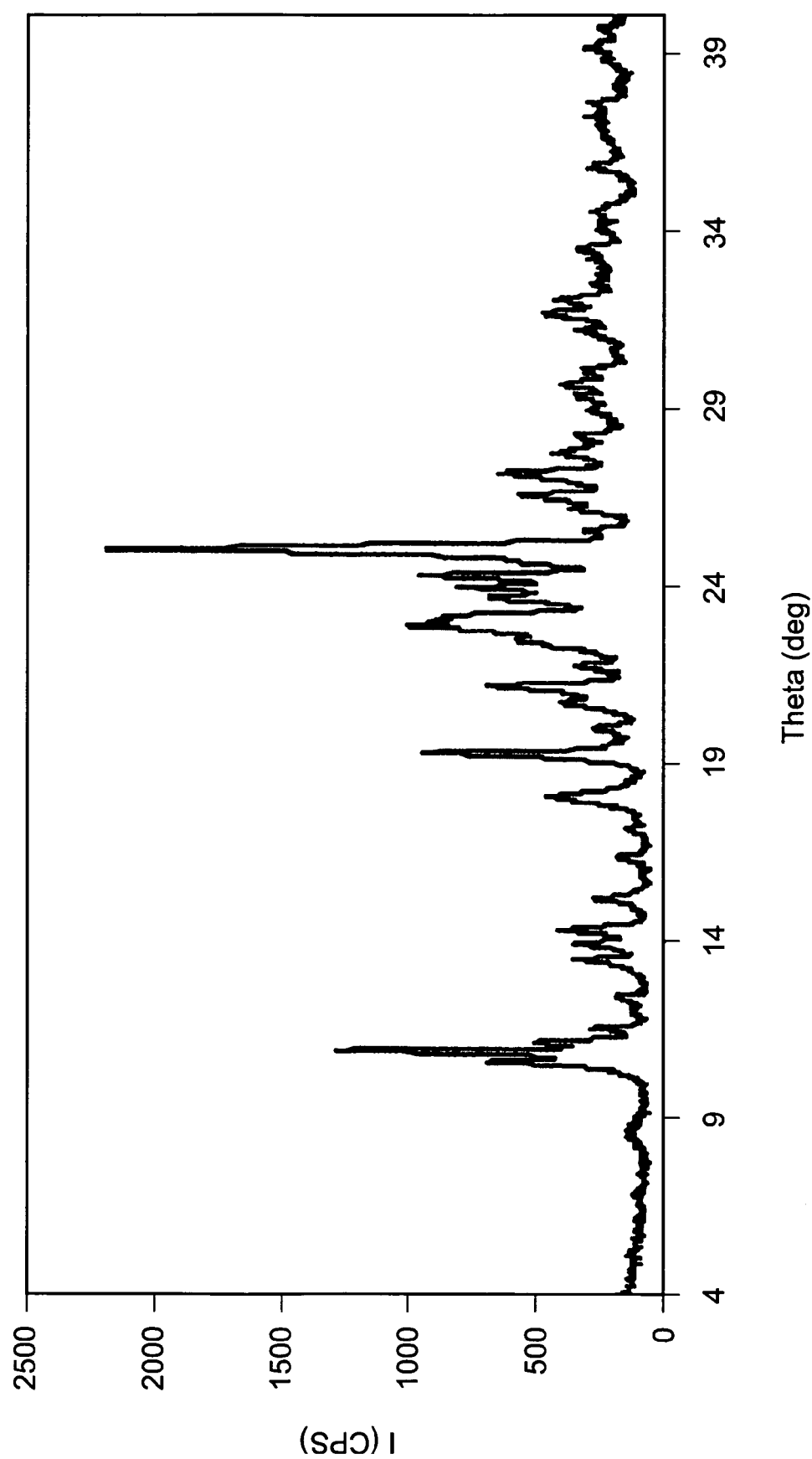
FIG. 1 is an X-ray powder diffraction diagram of polymorphic Form I (hydrate A) of the phosphate salt of 8-fluoro-2-{4-[(methylamino)methyl]phenyl}-1,3,4,5-tetrahydro-6H-azepino[5,4,3-cd]indol-6-one (Compound I).

It has surprisingly been found that the phosphate salt of 8-fluoro-2-{4-[(methylamino)methyl]phenyl}-1,3,4,5-tetrahydro-6H-azepino[5,4,3-cd]indol-6-one (Compound I) can exist in more than one polymorphic crystalline form. These forms may be used in a formulated product for the treatment of a mammalian disease condition mediated by poly(ADP-ribose) polymerase (PARP) activity, including cancer. Each form may have one or more advantages over the others in bioavailability, stability, or manufacturability. Crystalline polymorphic forms of Compound I have been discovered which are likely to be more suitable for bulk preparation and handling than other polymorphic forms. An amorphous form of Compound I is also provided. Processes for producing these polymorphic forms and amorphous form in high purity are described herein. Also provided are processes for the preparation of each polymorphic and amorphous form of Compound I, substantially free from other polymorphic forms of Compound I. Additionally, the invention provides pharmaceutical formulations comprising Compound I in different polymorphic forms and amorphous form as discussed above, and methods of treating a mammalian disease condition mediated by poly(ADP-ribose) polymerase (PARP) activity by administering such pharmaceutical formulations.

I. Polymorphic Forms of the Phosphate Salt of 8-Fluoro-2-{4-[(methylamino)methyl]phenyl}-1,3,4, 5-tetrahydro-6H-azepino[5,4,3-cd]indol-6-one (Compound I)

The present invention provides several polymorph crystalline forms of Compound I. Each crystalline form of Compound I can be characterized by one or more of the following: X-ray powder diffraction pattern (i.e., X-ray diffraction peaks at various diffraction angles (2θ)); melting point onset (and onset of dehydration for hydrated forms) as illustrated by endotherms of a Differential Scanning Calorimetry (DSC) thermogram; FT-IR spectral diagram pattern; Raman spectral diagram pattern; aqueous solubility; light stability under International Conference on Harmonization (ICH) high intensity light conditions; and physical and chemical storage stability. For example, samples of polymorphic Forms I, II, III, IV, V, and VI of Compound I were each characterized by the positions and relative intensities of peaks in their X-ray powder diffraction patterns. The X-ray powder diffraction parameters differ for each of the polymorphic Forms I, II, III, IV, V, and VI of Compound I. These polymorphic forms of Compound I can therefore be distinguished using X-ray powder diffraction.

The X-ray powder diffraction pattern for each polymorph form of the invention was measured on a Shimadzu XRD-6000 or Bruker Discover D8 X-ray diffractometer equipped with a Cu X-ray source operated at 40 kV and 30 mA or 40 kV and 40 mA, respectively. For the Shimadzu XRD-6000 X-ray diffractometer, the samples were placed in a sample holder and then packed and smoothed with a glass slide. During analysis, the samples were rotated at 60 rpm and analyzed from angles of 4 to 40 degrees (θ-2θ) at 5 degrees per minute with a 0.04 degree step or at 2 degrees per minute with a 0.02 degree step. If limited material was available, samples were placed on a silicon plate (zero background) and analyzed without rotation. The X-ray diffraction peaks, characterized by peak positions and intensity assignments, have been extracted from the X-ray powder diffractogram of each of the polymorphic forms of Compound I. For the Bruker Discover D8, the samples were placed on a glass slide and smoothed with a weighing paper. The samples were analyzed from angles of 4 to 40° (θ-2θ). One of skill in the art will appreciate that the peak positions (2θ) will show some inter-apparatus variability, typically as much as 0.1°. Accordingly, where polymorphic forms are described by characteristic X-ray powder diffraction peaks, the peak positions (2θ) should be understood as encompassing such variability. Similarly, where the solid forms of the present invention are described as having a X-ray powder diffraction pattern essentially the same as that shown in a given figure, the term "essentially the same" is intended to encompass such inter-apparatus variability in diffraction peak positions. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measures only.

Different polymorphic forms of Compound I were also distinguished using differential scanning calorimetry (DSC). DSC measures the difference in heat energy uptake between a sample solution and an appropriate reference solvent with increase in temperature. DSC thermograms are characterized by endotherms (indicating energy uptake) and also by exotherms (indicating energy release), typically as the sample is heated.

The DSC (Differential Scanning Calorimetry) thermographs were obtained using a TA instrument DSC Q1000 and Mettler Toledo DSC821e instrument at a scan rate of 5° C./min over a temperature range of 25-250° C. For DSC analysis, samples were weighed into aluminum hermetic pans that were sealed and punctured with a single hole. Depending on several factors, the endotherms exhibited by the compounds of the invention may vary by about 0.01-5° C. for crystal polymorph melting above or below the endotherms depicted in the appended figures. Factors responsible for such variance include the rate of heating (i.e., the scan rate) at which the DSC analysis is conducted, the way the DSC onset temperature is defined and determined, the calibration standard used, instrument calibration, the relative humidity and the chemical purity of the sample. For any given sample, the observed endotherms may also differ from instrument to instrument; however, it will generally be within the ranges defined herein provided the instruments are calibrated similarly.

Raman scattering spectra were obtained by using a Dispersive Raman Spectrometer from Kaiser Optical Instruments, Raman RXN1. The excitation light source was a 785-nm external-cavity-stabilized diode laser. The detector was a charge-coupled device (CCD). The resolution was 4 cm$^{-1}$.

The infrared spectra were recorded on a Bruker Vector33 FT-IR spectrophotometer. Sample of drug substance was ground with potassium bromide and pressed into a pellet. The pellet was scanned from 4000 cm$^{-1}$ to 400 cm$^{-1}$. Major peaks were marked between 3400$^{-1}$ to 500 cm$^{-1}$.

Different polymorphic forms of Compound I may also be distinguished by different stabilities and different solubilities.

In one embodiment, the polymorphic forms of the present invention are substantially pure, meaning each polymorphic form of Compound I includes less than 10%, for example less than 5%, or for example less than 3%, or even further, for example, less than 1% by weight of impurities, including other polymorphic forms of Compound I.

The solid forms of the present invention may also comprise more than one polymorphic form. One of skill in the art will recognize that crystalline forms of a given compound can exist in substantially pure forms of a single polymorph, and can also exist in a crystalline form that comprises two or more different polymorphs. Where a solid form comprises two or more polymorphs, the X-ray diffraction pattern will have peaks characteristic of each of the individual polymorphs of the present invention. For example, a solid form that comprises two polymorphs will have a X-ray powder diffraction pattern that is a convolution of the two X-ray diffraction patterns that correspond to the substantially pure polymorphic forms. In one embodiment, for example, a solid form of the present invention containing a first and second polymorphic form contains at least 10% of the first polymorph. In a further embodiment, the solid form contains at least 20% of the first polymorph. Even further embodiments contain at least 30%, at least 40%, or at least 50% of the first polymorph. One of skill in the art will recognize that many such combinations of several individual polymorphs in varying amounts are possible.

In the following discussion, X-ray diffraction and infrared absorption data are given for various polymorphs. Although the measured diffraction angles are reported to two decimal places, it should be appreciated that the accuracy of the diffraction angles is ±0.1°, as described above.

A. Polymorphic Form IV (Methanol Solvate)

Polymorphic Form IV of Compound I can be prepared by phosphorylation of the compound 8-fluoro-2-{4-[(methylamino)methyl]phenyl}-1,3,4,5-tetrahydro-6H-azepino[5,4,3-cd]indol-6-one represented by formula 1 in methanol.

Polymorphic Form IV of Compound I is physically and chemically stable at 40° C. under 75% relative humidity for at least 3 months.

Polymorphic Form IV of Compound I has an aqueous solubility of 4.5 mg/mL at pH 5.4.

Figure 10:
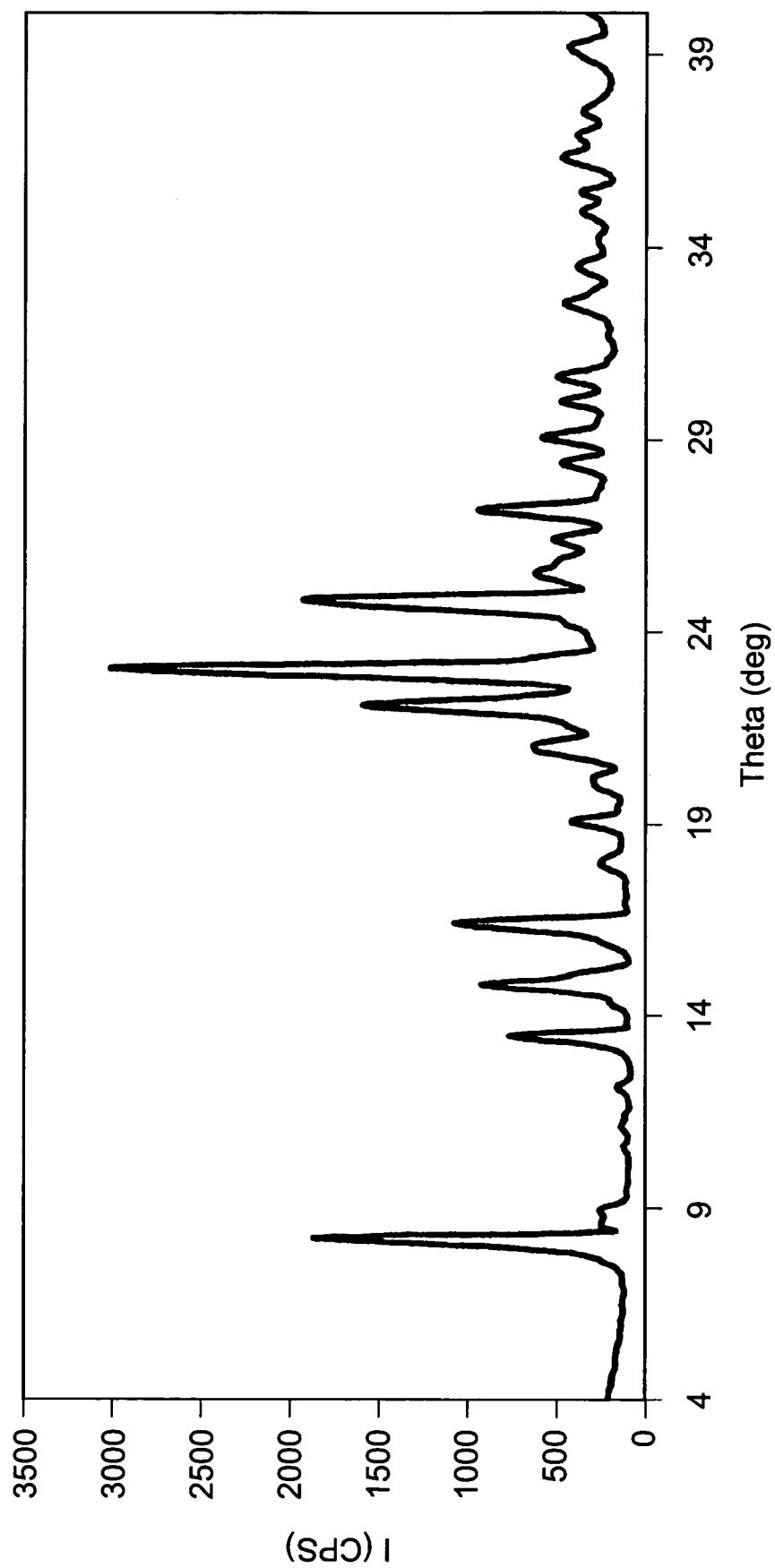
FIG. 10 is an X-ray powder diffraction diagram of polymorphic Form IV (MeOH solvate) of Compound I.

The X-ray powder diffraction pattern of Form IV was measured as described herein, with peaks found at the following approximate diffraction angles (2θ): 8.20, 13.52, 14.88, 16.48, 18.08, 19.14, 20.26, 21.06, 22.08, 23.00, 24.80, 25.54, 26.42, 27.14, 28.36, 29.02, 29.92, 30.58, 32.48, 33.42, 34.8, 35.32, 36.22, 36.78, 37.44, 39.08. FIG. 10 provides an X-ray powder diffraction pattern for Form IV.

Figure 11:
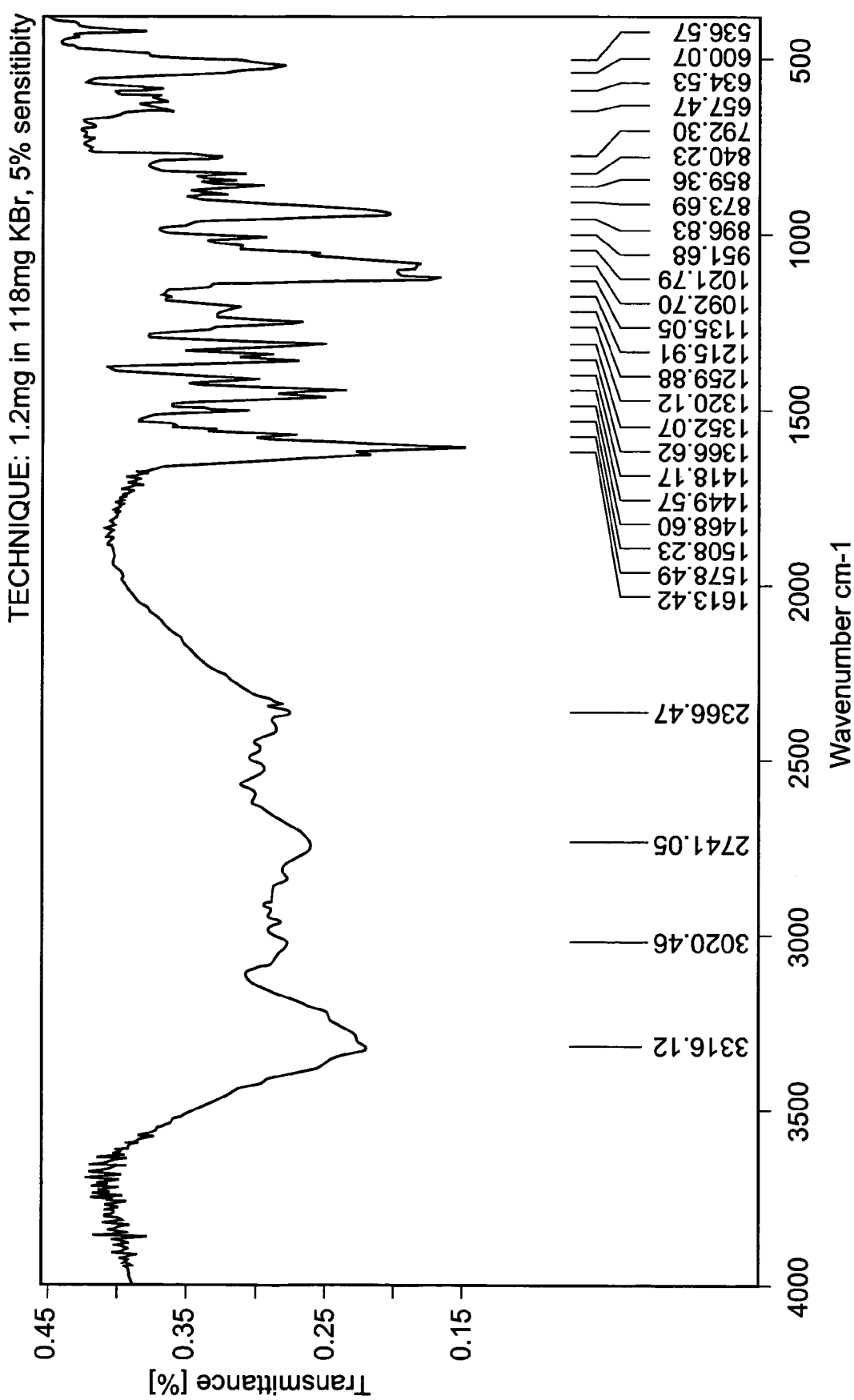
FIG. 11 is an infrared absorption spectrum of polymorphic Form IV (MeOH solvate) of Compound I.

The infrared absorption spectrum of Form IV was measured as described herein, with bands found at the following approximate positions (cm$^{-1}$): 536.57, 600.07, 634.53, 657.47, 792.30, 840.23, 859.36, 873.69, 896.83, 951.68, 1021.79, 1092.70, 1135.05, 1215.91, 1259.88, 1320.12, 1352.07, 1366.62, 1418.17, 1449.57, 1468.60, 1508.23, 1578.49, 1613.42, 2366.47, 2741.05, 3020.46, 3316.12. FIG. 11 provides an infrared absorption spectrum of polymorphic Form IV.

Figure 12:
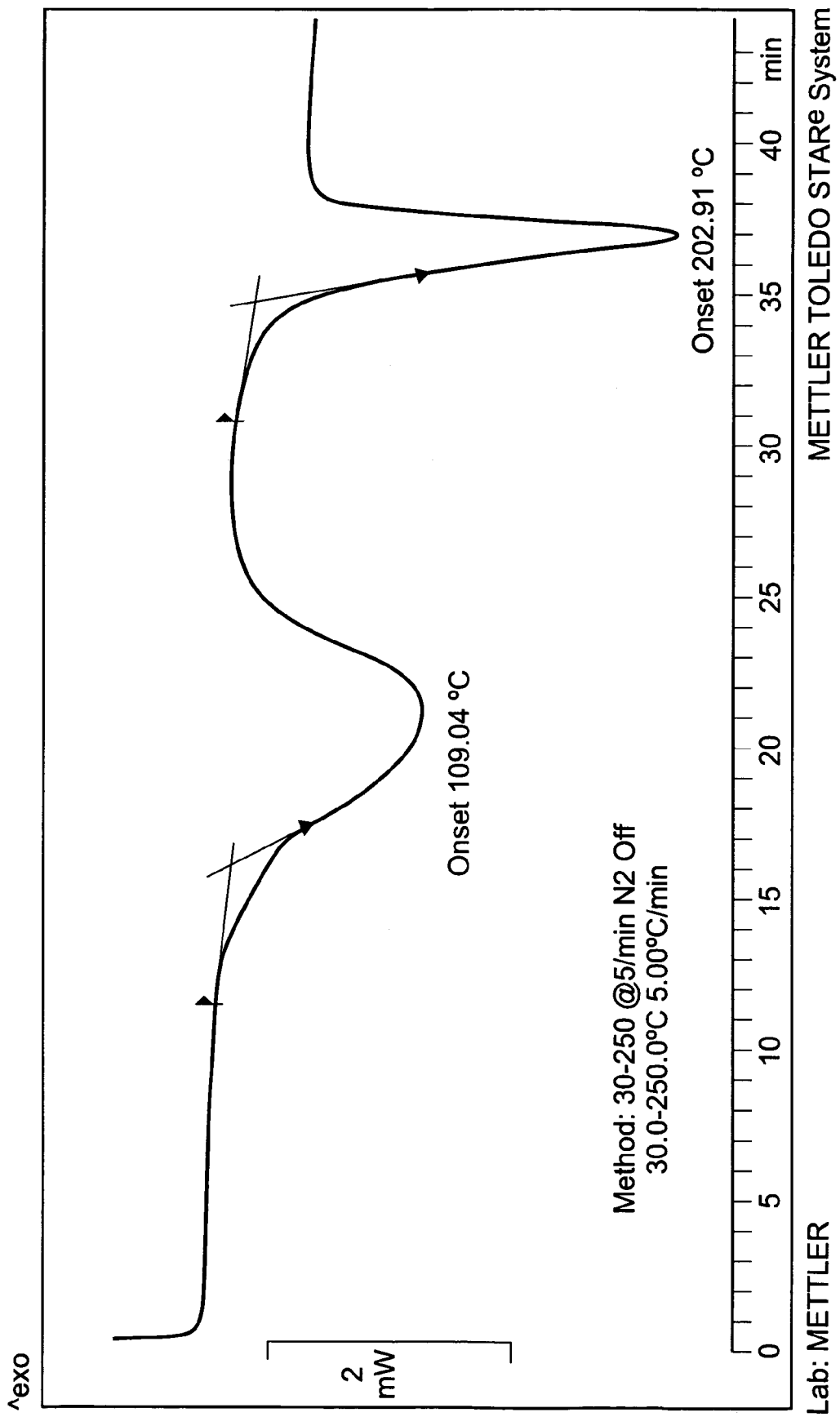
FIG. 12 is a differential scanning calorimetry (DSC) profile of polymorphic Form IV (MeOH solvate) of Compound I. A typical profile displays an endotherm with onset at 204° C. at a scan rate of 5° C./minute.

The DSC thermogram for Form IV, shown in FIG. 12, indicates an endotherm onset at 204.0° C. at a scan rate of 5° C./minute.

B. Polymorphic Form I (Hydrate A)

Polymorphic Form I of Compound I is a hydrate. Polymorphic Form I of Compound I can be produced by treating polymorphic Form IV (MEOH solvate) with water.

Polymorphic Form I of Compound I is chemically stable at 40° C. under 75% relative humidity for at least 3 months, but it will be converted to Form III (Hydrate B) after one week at this condition. Form I is physically stable at ambient condition for at least 3 months.

Polymorphic Form I of Compound I has an aqueous solubility of 2.8 mg/mL at pH 5.4.

The X-ray powder diffraction pattern of Form 1 was measured as described herein, with peaks found at the following approximate diffraction angles (2θ): 10.56, 10.88, 11.14, 11.54, 13.46, 13.90, 14.30, 15.20, 16.34, 17.12, 18.02, 19.30, 20.02, 20.72, 21.22, 21.76, 22.50, 22.94, 23.70, 24.00, 24.32, 25.02, 25.54, 26.22, 26.60, 27.20, 27.76, 29.02, 29.38, 29.74, 31.26, 31.76, 32.12, 33.52, 35.78. FIG. 1 provides an X-ray powder diffraction pattern for Form I.

Figure 2:
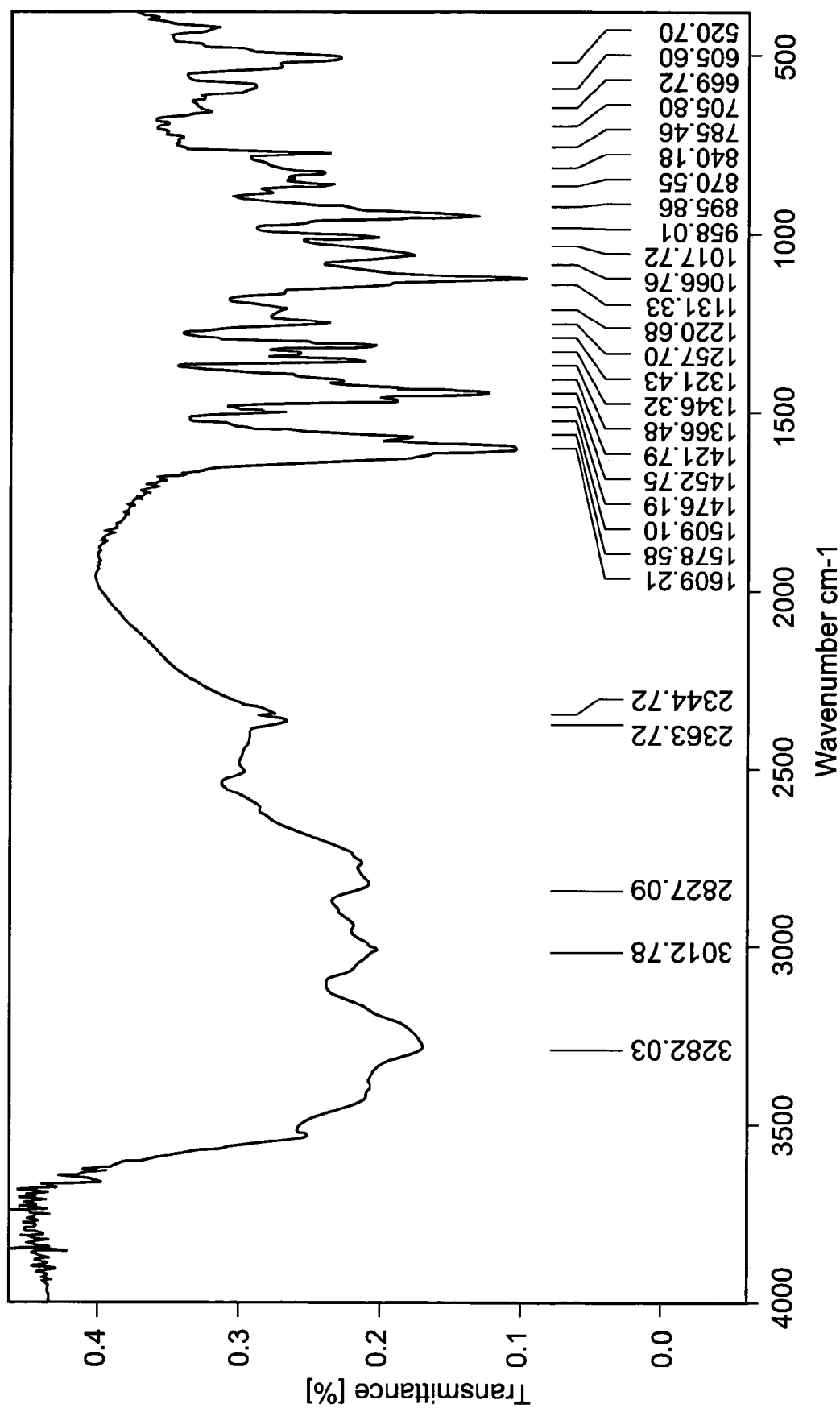
FIG. 2 is an infrared absorption spectrum of polymorphic Form I (hydrate A) of Compound I.

The infrared absorption spectrum of Form I was measured as described herein, with bands found at the following approximate positions (cm$^{-1}$): 520.70, 605.60, 669.72, 705.80, 785.46, 840.18, 870.55, 895.86, 958.01, 1017.72, 1066.76, 1131.33, 1220.68, 1257.70, 1321.43, 1346.32, 1366.48, 1421.79, 1452.75, 1476.19, 1509.10, 1578.58, 1609.21. FIG. 2 provides an infrared absorption spectrum of polymorphic Form I.

Figure 3:
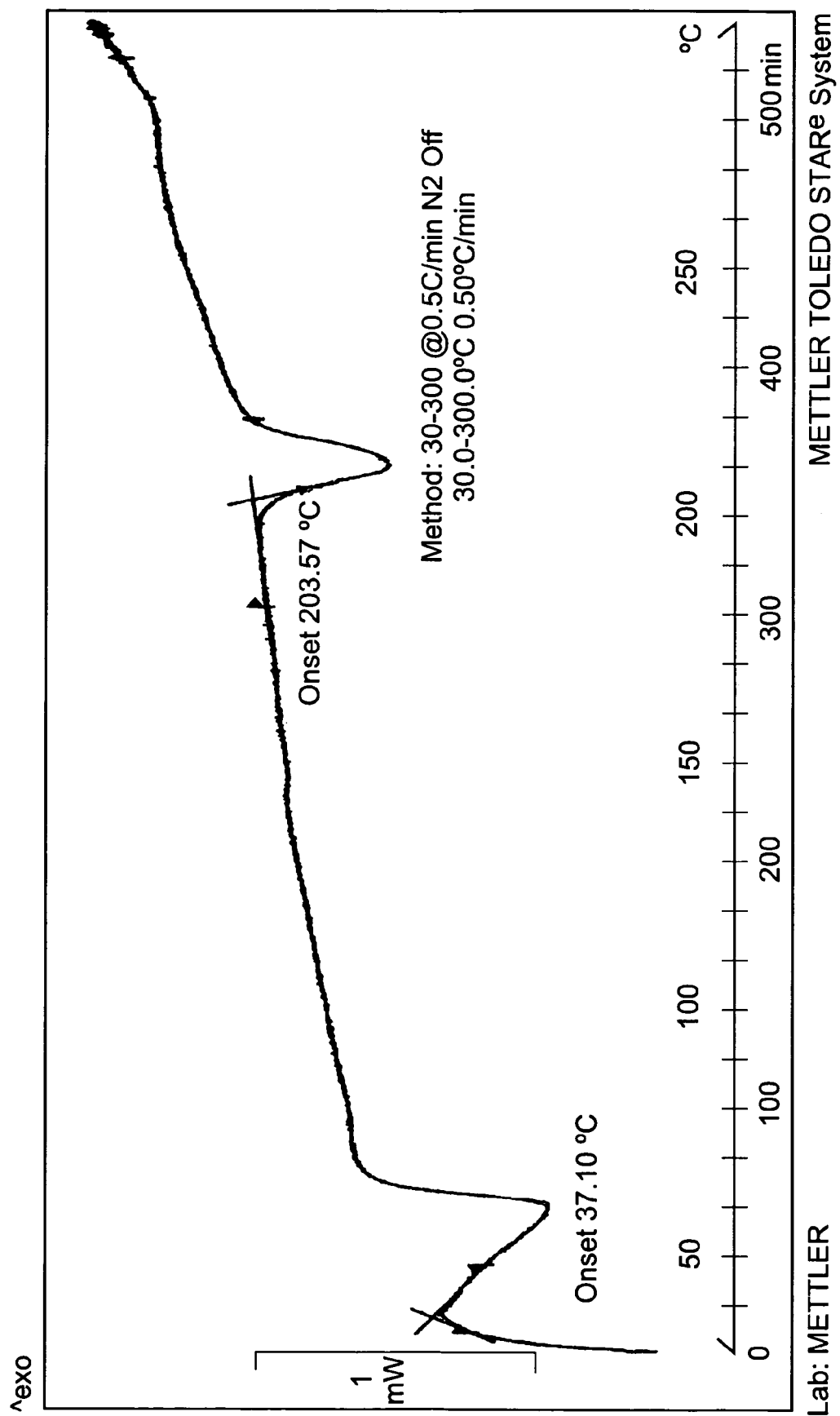
FIG. 3 is a differential scanning calorimetry (DSC) profile of polymorphic Form I (hydrate A) of Compound I. A typical profile displays an endotherm with onset at 202° C. at a scan rate of 5° C./minute.

The DSC thermogram for Form I, shown in FIG. 3, indicates an endotherm onset at 202° C. at a scan rate of 5° C./minute.

C. Polymorphic Form II (Anhydrous Form)

Polymorphic Form II of Compound I is an anhydrous form. Form II can be produced by dehydration of Form I.

Polymorphic Form II of Compound I is physically stable at ambient condition for at least 3 months. Form II can be converted to Form III (Hydrate B) at 40° C. under 75% relative humidity after 1 week or at 25° C. under 90% relative humidity overnight.

Figure 15:
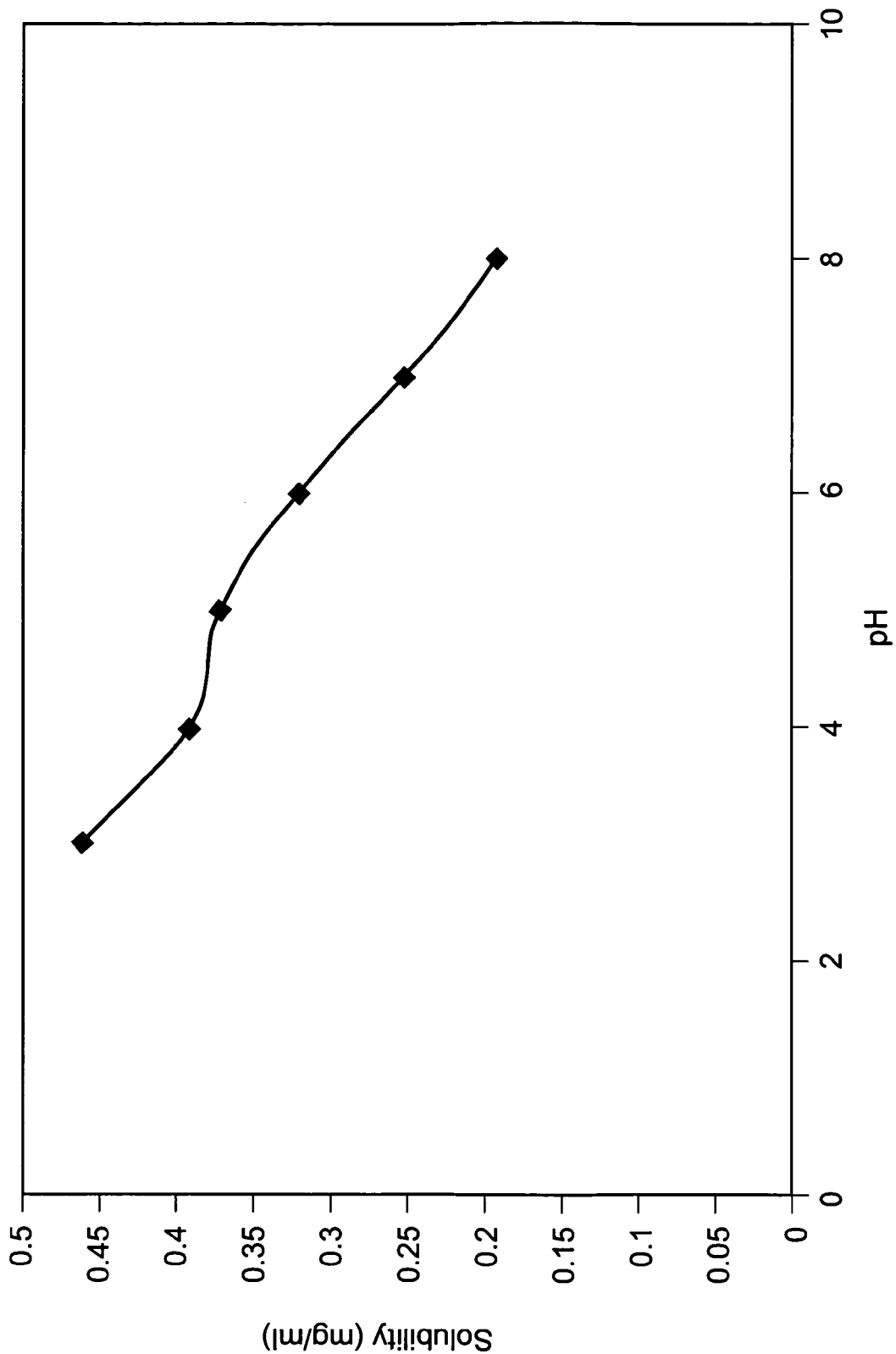
FIG. 15 is a pH solubility profile of polymorphic Form II (anhydrous form) of Compound I.

Polymorphic Form II of Compound I has an aqueous solubility of 3.0 mg/mL at pH 5.4. The pH solubility study of Form II was conducted at pH range 3.0 to 8.0. The buffer systems used in this study are 50 mM ammonium phosphate for pH 3.0 and 4.0, and 50 mM sodium phosphate buffer for pH 5.0 to 8.0. The solubility results are shown in Table 1 and FIG. 15. It could be seen that the solubility of Form II decreases with the increase of pH from 3.0 to 8.0. Because Form II is a phosphate salt and phosphate buffers were used in the pH solubility study, the solubility determined in these buffer systems are lower than the solubility in water due to the common ion effect.

TABLE 1 pH Solubility Profile of Form II

| Buffer pH | Solubility (mg/mL) |
| --- | --- |
| 3 | 0.46 |
| 4 | 0.39 |
| 5 | 0.37 |
| 6 | 0.32 |
| 7 | 0.25 |
| 8 | 0.19 |

Figure 4:
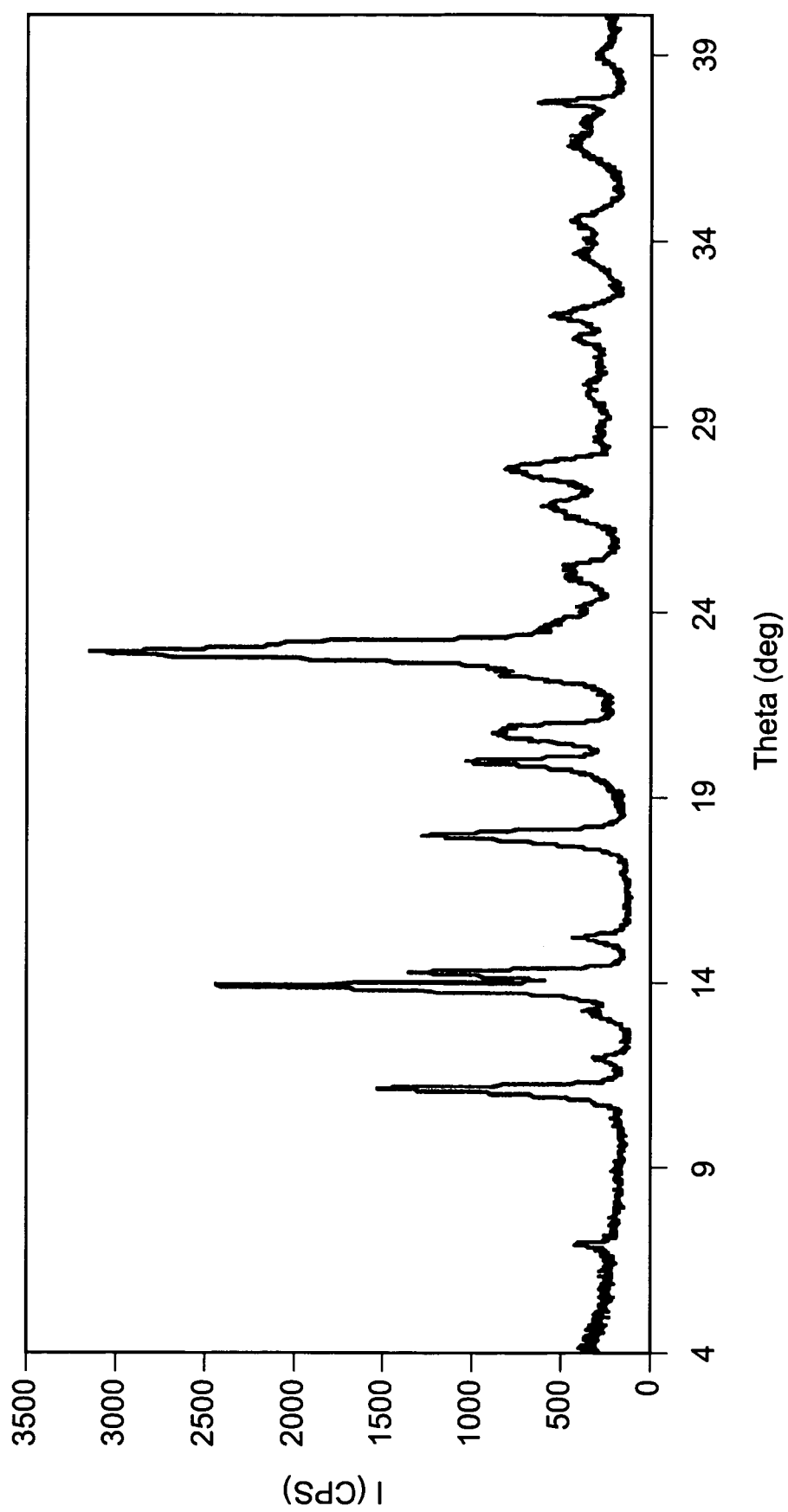
FIG. 4 is an X-ray powder diffraction diagram of polymorphic Form II (anhydrous form) of Compound I.

The X-ray powder diffraction pattern of Form II was measured as described herein, with peaks found at the following approximate diffraction angles (2θ): 7.02, 11.22, 12.12, 14.00, 14.44, 15.36, 18.12, 20.12, 20.92, 22.52, 23.12, 25.28, 26.96, 28.00, 30.02, 31.40, 32.04, 33.72, 34.62, 36.66, 37.26, 39.04. FIG. 4 provides an X-ray powder diffraction pattern for Form II.

Figure 5:
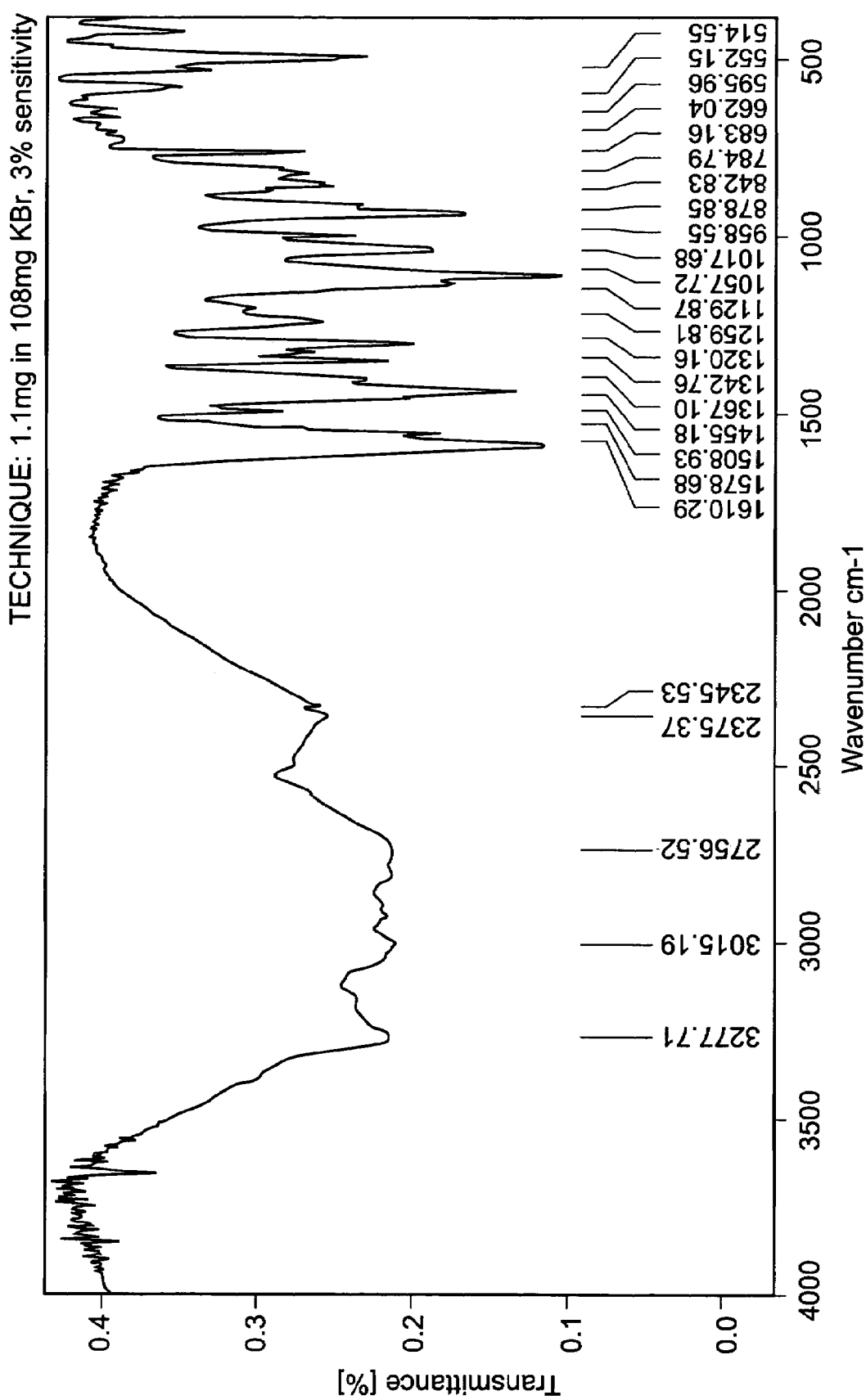
FIG. 5 is an infrared absorption spectrum of polymorphic Form II (anhydrous form) of Compound I.

The infrared absorption spectrum of Form II was measured as described herein, with bands found at the following approximate positions (cm$^{-1}$): 514.55, 552.15, 595.96, 662.04, 683.16, 784.79, 842.83, 878.85, 958.55, 1017.68, 1057.72, 1129.87, 1259.81, 1320.16, 1342.76, 1367.10, 1455.18, 1508.93, 1578.68, 1610.29, 2345.53, 2375.37, 2756.52, 3015.19, 3277.71. FIG. 5 provides an infrared absorption spectrum of polymorphic Form II.

Figure 6:
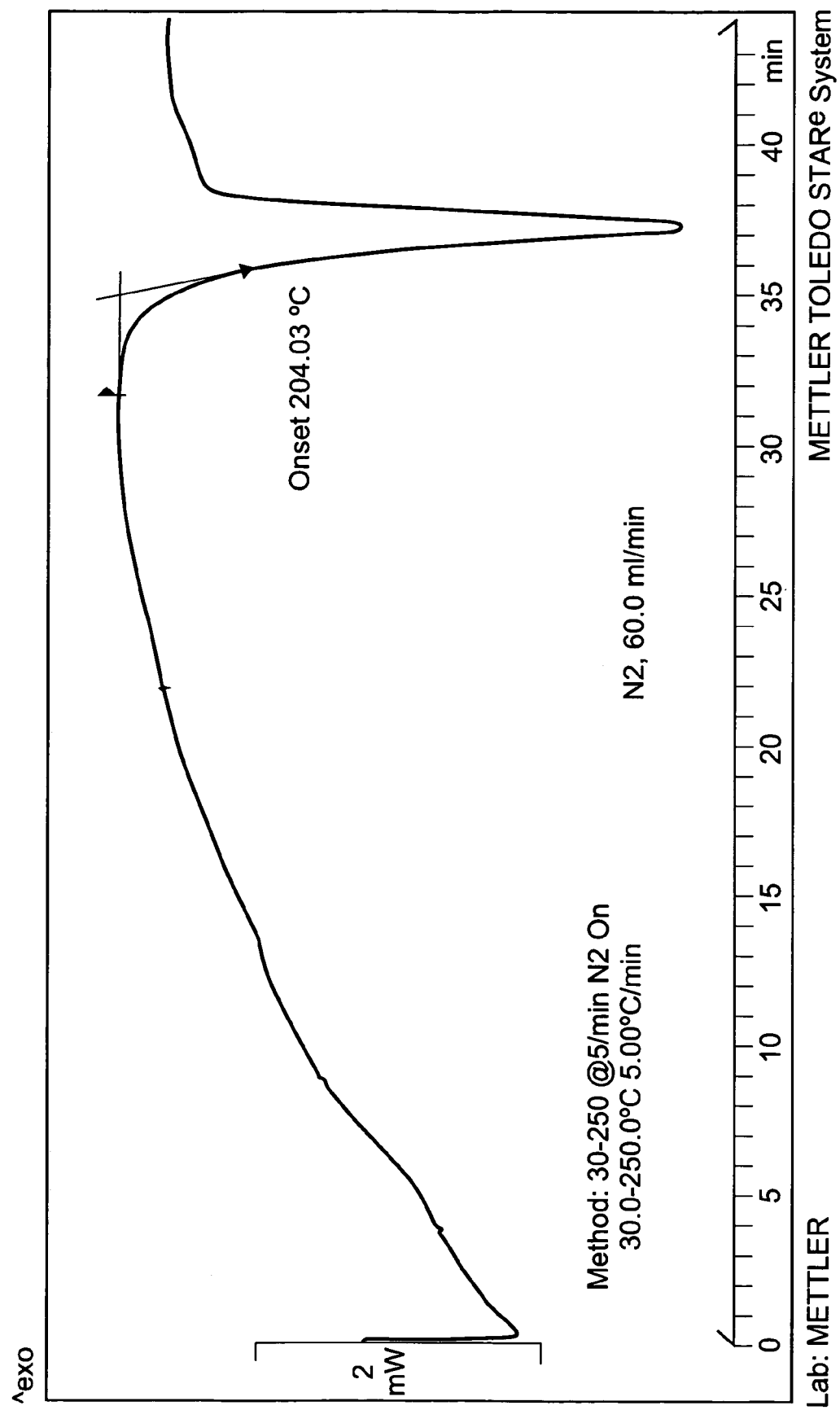
FIG. 6 is a differential scanning calorimetry (DSC) profile of polymorphic Form II (anhydrous form) of Compound I. A typical profile displays an endotherm with onset at 205° C. at a scan rate of 5° C./minute.

The DSC thermogram for Form II, shown in FIG. 6, indicates an endotherm onset at 205° C. at a scan rate of 5° C./minute.

D. Polymorphic Form III (Hydrate B)

Polymorphic Form III of Compound I is a hydrate. Polymorphic Form III of Compound I can be produced by hydration of Form I or Form II.

Polymorphic Form III of Compound I is physically and chemically stable at 40° C. under 75% relative humidity for at least 3 months.

Polymorphic Form III of Compound I has an aqueous solubility of 2.7 mg/mL at pH 5.4.

Figure 7:
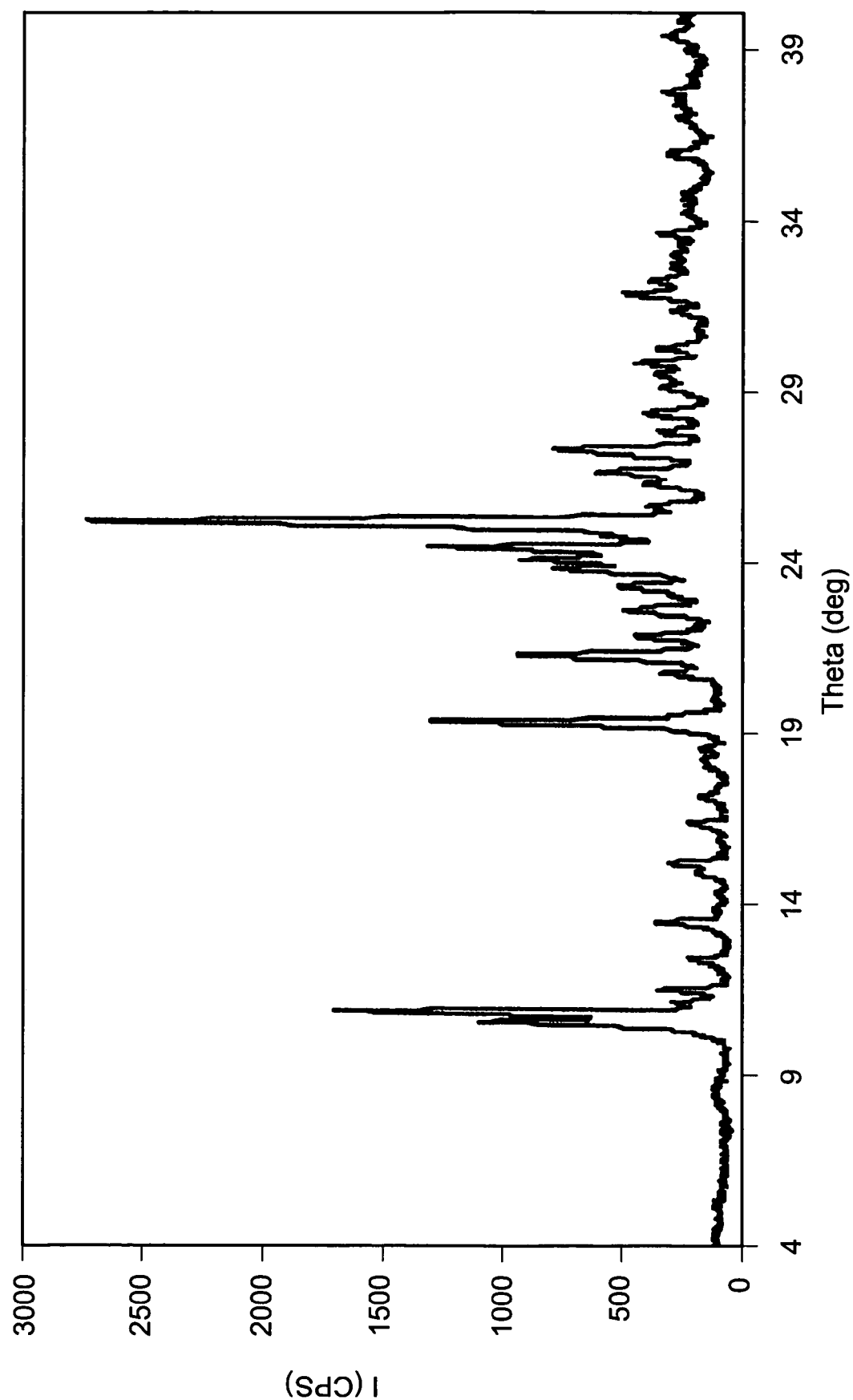
FIG. 7 is an X-ray powder diffraction diagram of polymorphic Form III (hydrate B) of Compound I.

The X-ray powder diffraction pattern of Form III was measured as described herein, with peaks found at the following approximate diffraction angles (2θ): 10.66, 10.96, 11.62, 13.54, 15.28, 16.42, 19.36, 20.80, 21.30, 21.86, 22.56, 23.28, 23.78, 24.06, 24.42, 25.12, 26.30, 26.62, 27.32, 27.84, 28.32, 29.10, 29.50, 29.80, 30.24, 31.84, 32.20, 32.58, 35.86. FIG. 7 provides an X-ray powder diffraction pattern for Form III.

Figure 8:
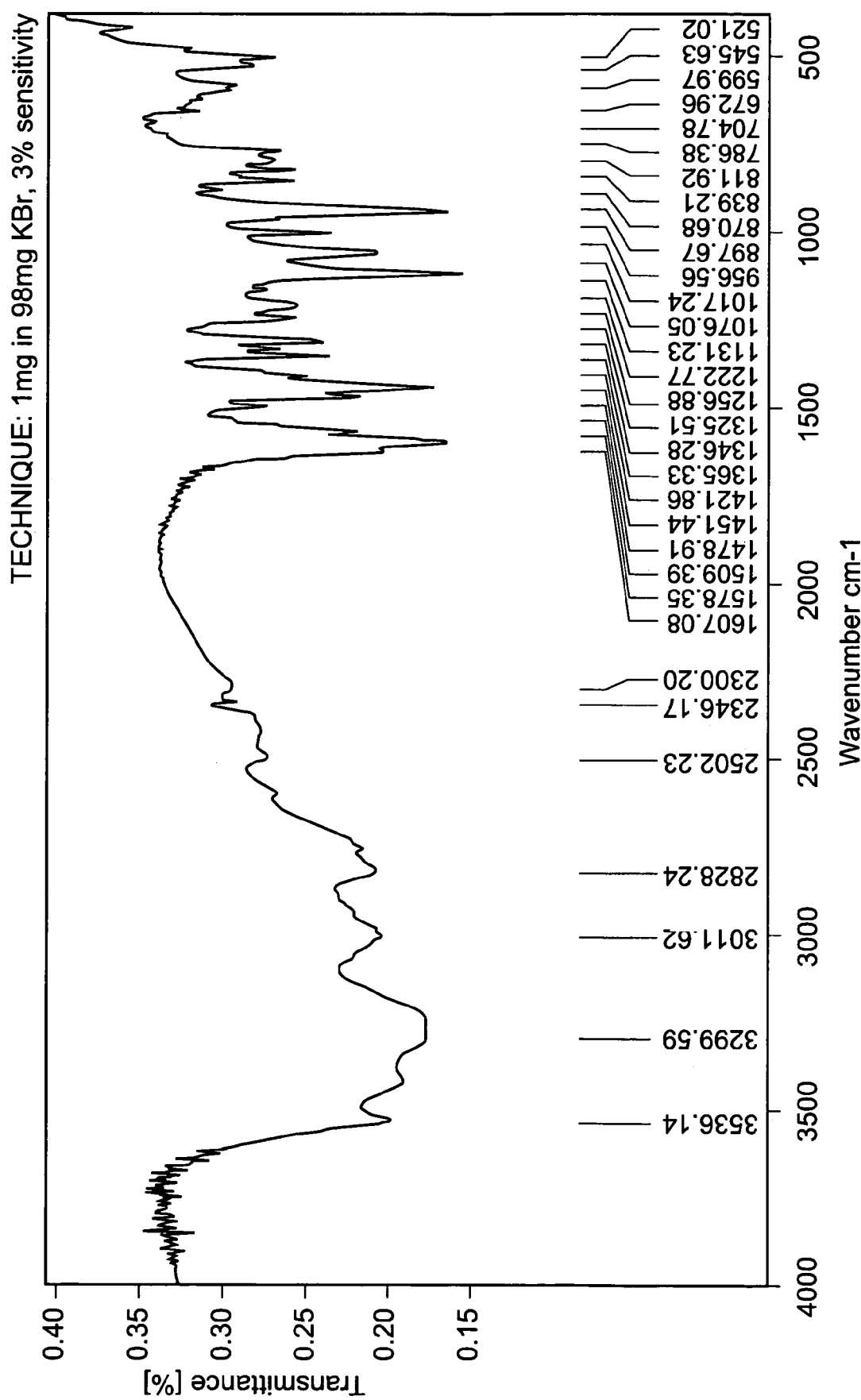
FIG. 8 is an infrared absorption spectrum of polymorphic Form III (hydrate B) of Compound I.

The infrared absorption spectrum of Form III was measured as described herein, with bands found at the following approximate positions (cm$^{-1}$): 521.02, 545.63, 599.97, 672.96, 704.78, 786.38, 811.92, 839.21, 870.68, 897.67, 956.56, 1017.24, 1076.05, 1131.23, 1222.77, 1256.88, 1325.51, 1346.28, 1365.33, 1421.86, 1451.44, 1478.91, 1509.39, 1578.35, 1607.08, 2300.20, 2346.17, 2502.23, 2828.24, 3011.62, 3299.59, 3536.14. FIG. 8 provides an infrared absorption spectrum of polymorphic Form III.

Figure 9:
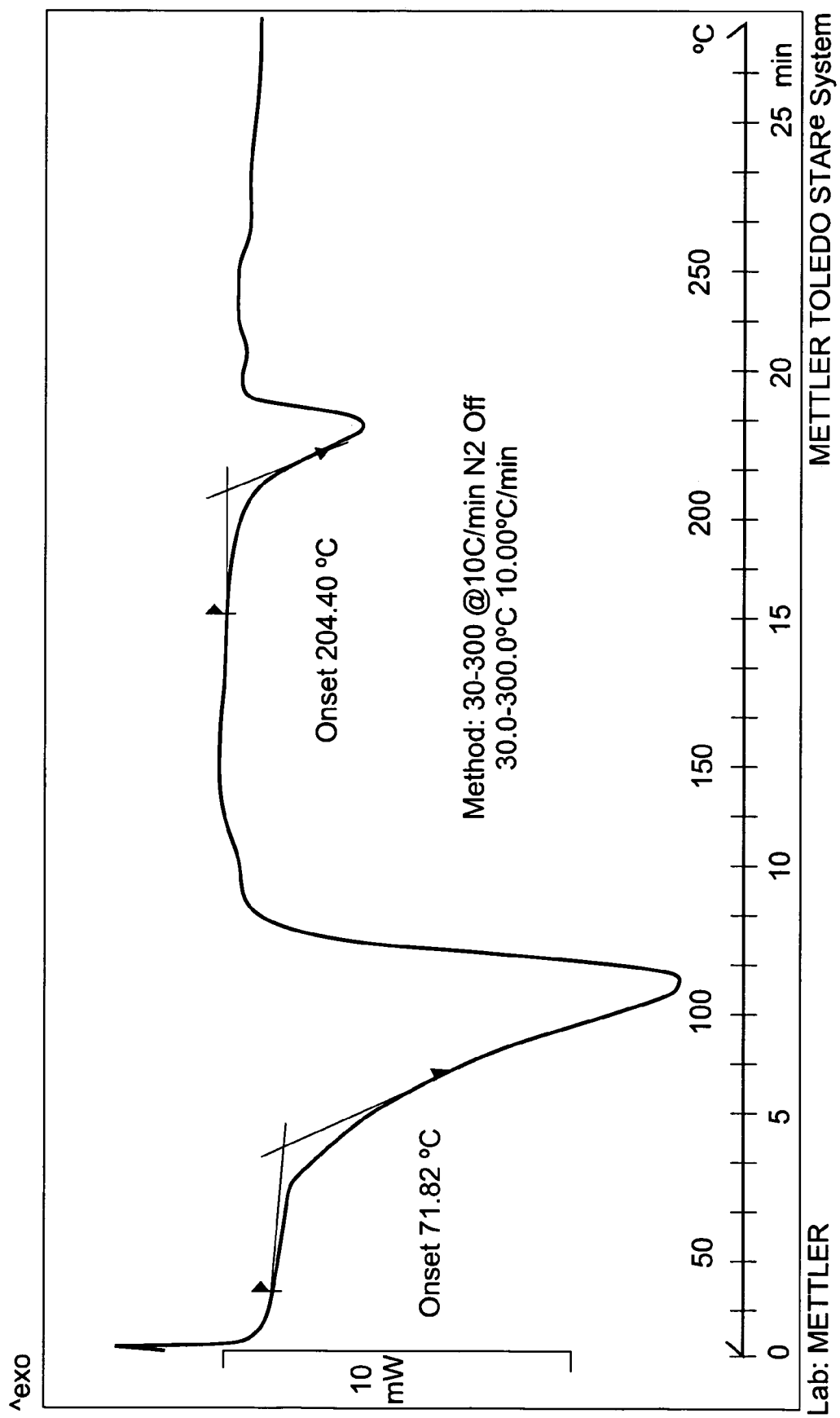
FIG. 9 is a differential scanning calorimetry (DSC) profile of polymorphic Form III (hydrate B) of Compound I. A typical profile displays an endotherm with onset at 203° C. at a scan rate of 5° C./minute.

The DSC thermogram for Form III, shown in FIG. 9, indicates an endotherm onset at 203° C. at a scan rate of 5° C./minute.

E. Polymorph Form V (Hydrate C)

Polymorphic Form V of Compound I was formed during the stability studies of Form II when stored at 40° C. under 75% relative humidity for 6 months period. Polymorphic Form V of Compound I is physically and chemically stable at room temperature for at least 3 months.

Polymorphic Form V of Compound I has an aqueous solubility of 3.0 mg/mL at pH 5.4.

Figure 13:
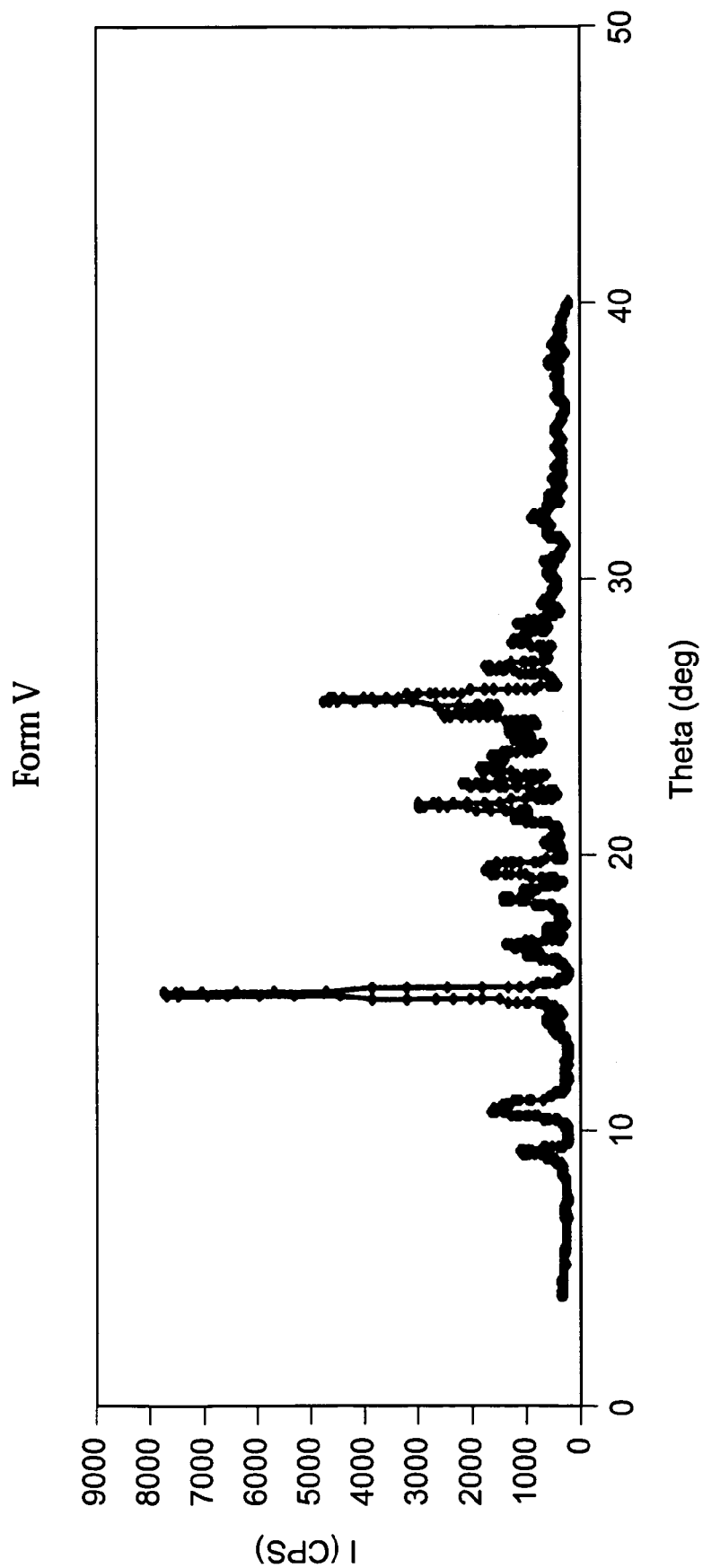
FIG. 13 is an X-ray powder diffraction diagram of polymorphic Form V (hydrate C) of Compound I.

The X-ray powder diffraction pattern of Form V was measured as described herein, with peaks found at the following approximate diffraction angles (2θ): 8.64, 9.05, 10.26, 10.56, 10.84, 13.88, 14.85, 15.24, 16.24, 16.59, 17.07, 18.26, 18.56, 19.26, 19.56, 20.31, 21.16, 21.61, 22.38, 22.96, 23.40, 24.04, 24.34, 24.92, 25.46, 25.78, 26.22, 26.59, 27.10, 27.60, 27.88, 28.24, 29.03, 30.08, 30.44, 31.54, 32.08, 32.52, 36.45, 36.90, 37.14, 37.58, 37.74, 38.30, 39.00. FIG. 13 provides an X-ray powder diffraction pattern of Form V.

Figure 16:
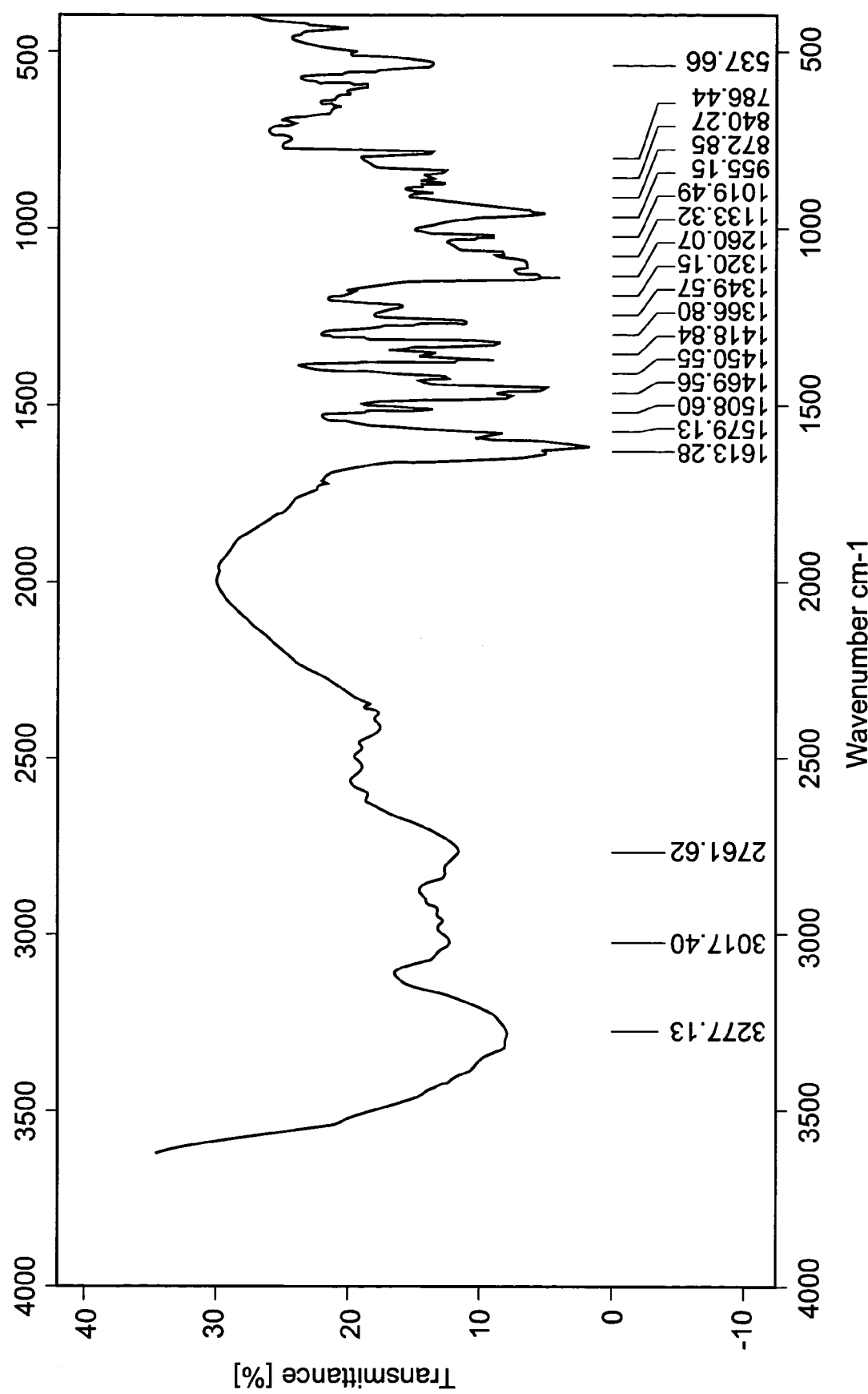
FIG. 16 is an infrared absorption spectrum of polymorphic Form V (hydrate C) of Compound I.

The infrared absorption spectrum of Form V was measured as described herein, with bands found at the following approximate positions (cm$^{-1}$): 955.28, 1019.70, 1045.84, 1067.25, 1092.06, 1104.99, 1133.50, 1260.13, 1320.27, 1366.85, 1418.85, 1450.75, 1470.01, 1579.05, 1613.39, 1632.61, 2761.48, 3024.44, 3278.09, 3312.93. FIG. 16 provides an infrared absorption spectrum of polymorphic Form V.

Figure 17:
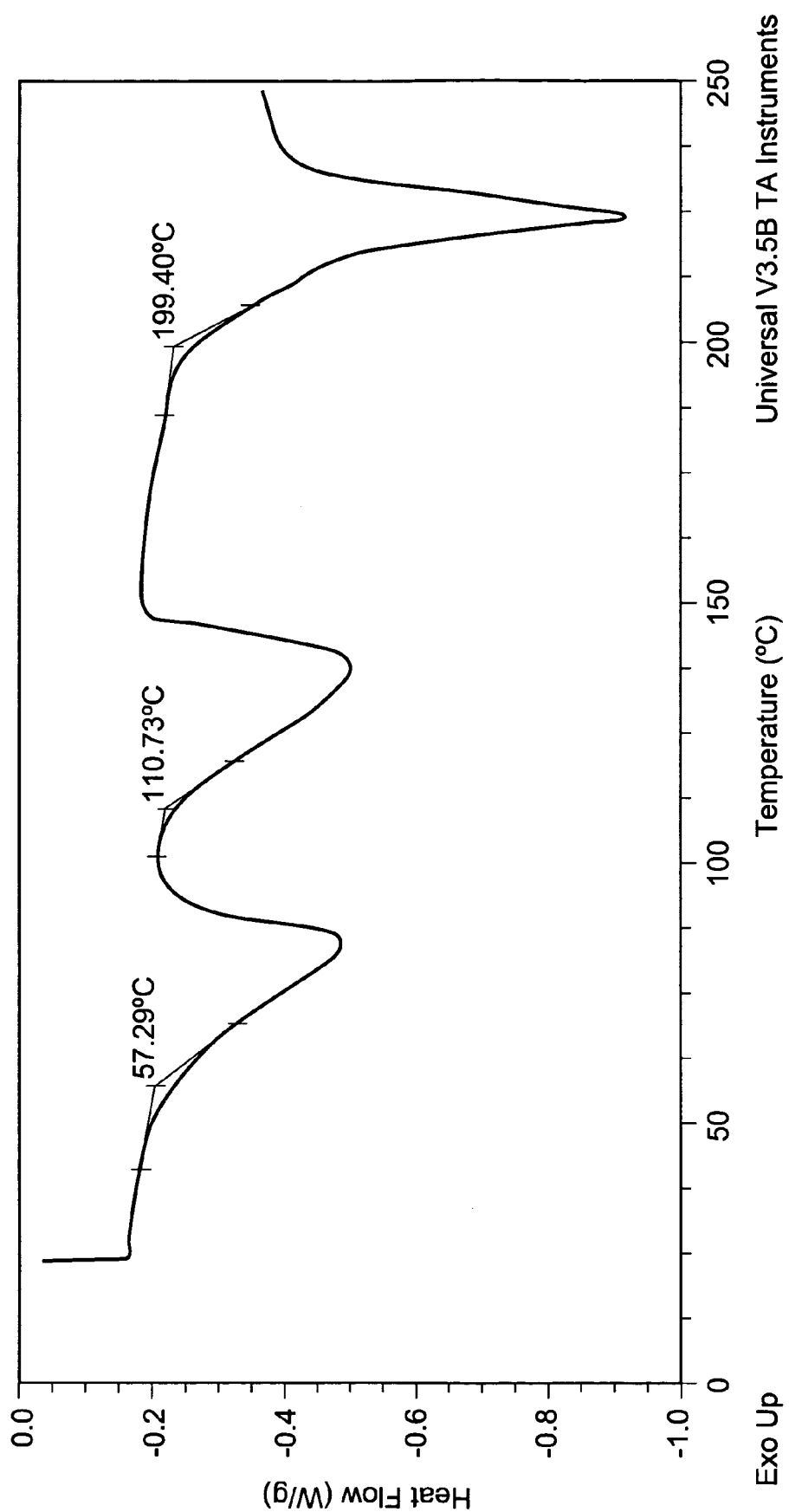
FIG. 17 is a differential scanning calorimetry (DSC) profile of polymorphic Form V (hydrate C) of Compound I.

The DSC thermogram for Form V, shown in FIG. 17, has an endotherm at 199.40° C., with two desolvation peaks at 57.29° C. and 110.73° C., respectively.

F. Polymorph Form VI

Figure 14:
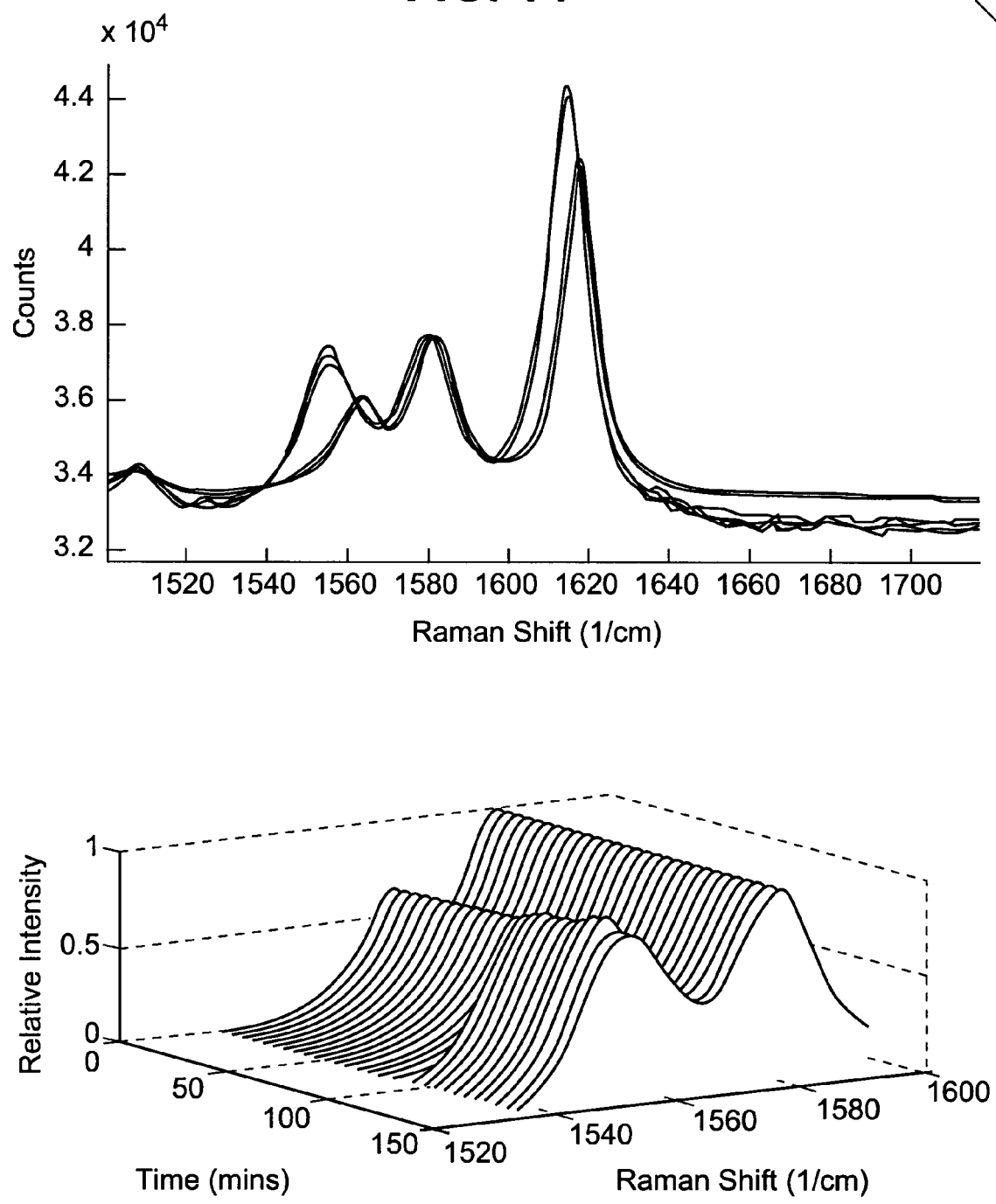
FIG. 14 is an aqueous slurry Raman study of polymorphic Form V (hydrate C) of Compound I.

Polymorphic Form VI of Compound I can be prepared by taking an aqueous slurry of Form II and heating at 100° C. overnight. As shown in FIG. 14, conversion began at 80° C. and was complete following the overnight hold at 100° C.

Figure 18:
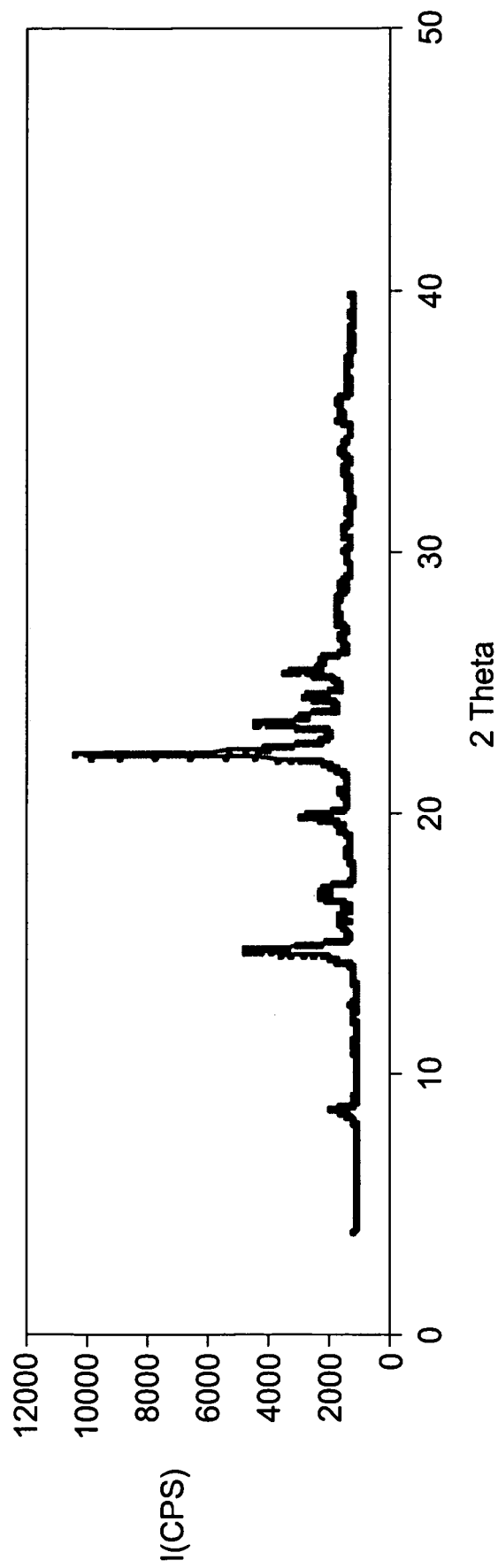
FIG. 18 is an X-ray powder diffraction diagram of polymorphic Form VI of Compound I.

The X-ray powder diffraction pattern of Form VI was measured as described herein, with peaks found at the following approximate diffraction angles (2θ): 8.44, 8.71, 14.78, 15.10, 15.73, 16.06, 16.24, 16.9, 17.2, 19.99, 22.32, 22.60, 22.94, 23.49, 23.84, 24.55, 25.30, 25.48, 27.74, 26.02, 27.47, 27.84, 28.10, 28.40, 34.02, 35.12, 35.54, 35.88. FIG. 18 provides an X-ray powder diffraction diagram of polymorphic Form VI.

Figure 19:
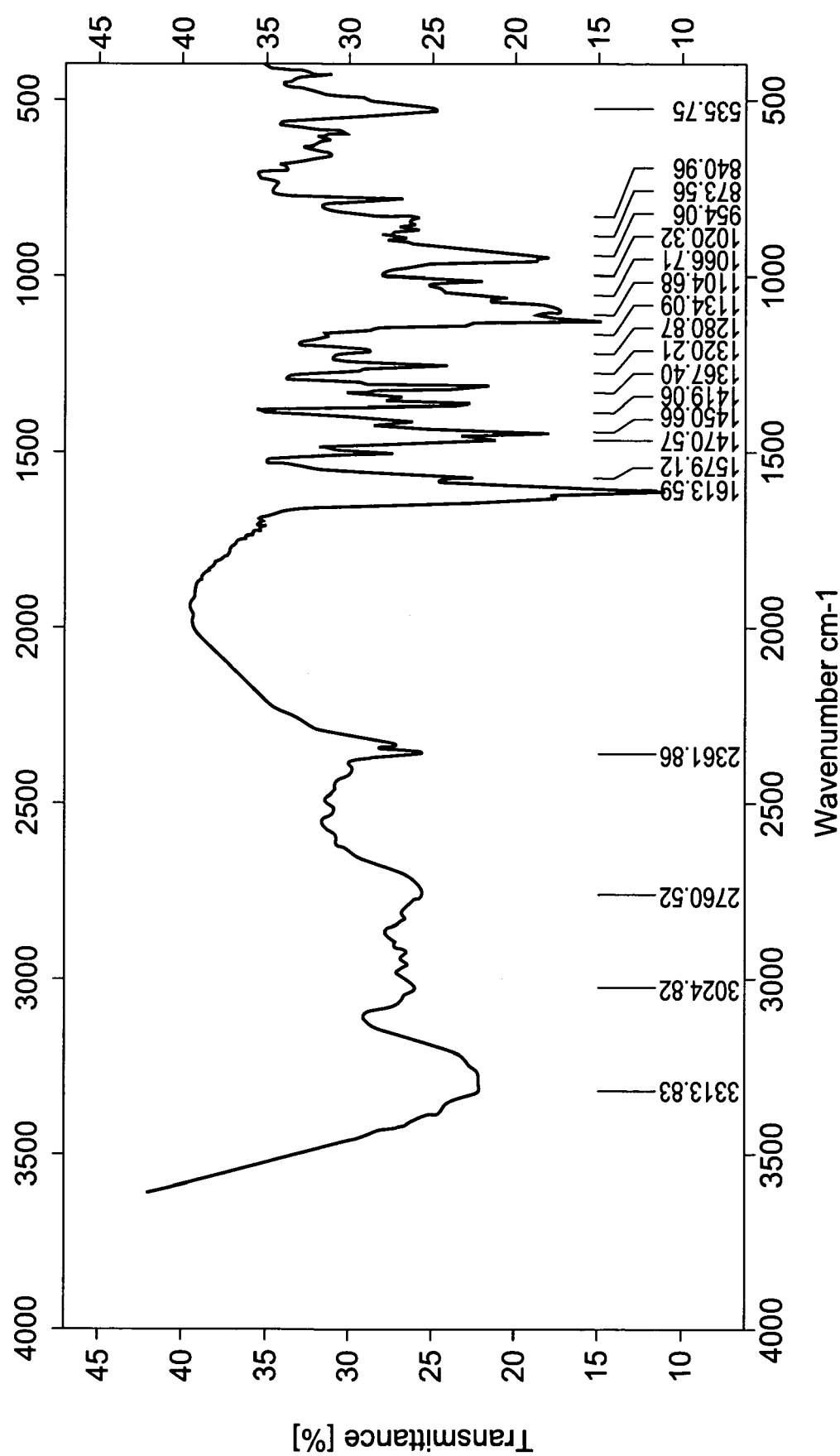
FIG. 19 is an infrared absorption spectrum of polymorphic Form VI of Compound I.

The infrared absorption spectrum of Form VI was measured as described herein, with bands found at the following approximate positions (cm$^{-1}$): 535.82, 786.11, 841.00, 954.18, 1020.17, 1133.96, 1216.98, 1260.79, 1320.11, 1367.35, 1418.66, 1450.88, 1470.60, 1508.44, 1579.24, 1613.51, 2410.94, 2760.82, 3025.77, 3277.18. FIG. 19 provides an infrared absorption spectrum of polymorphic Form VI.

Figure 20:
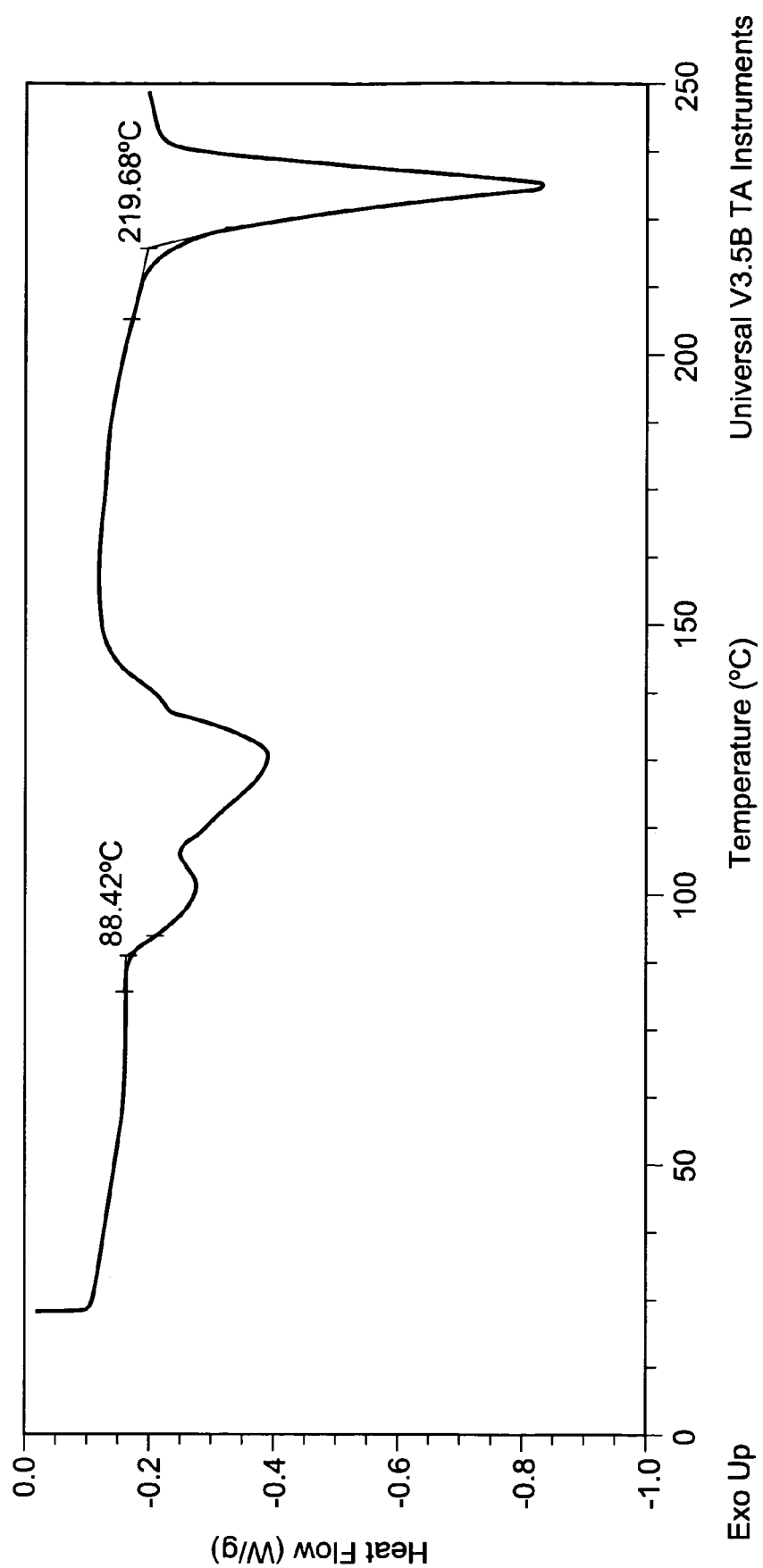
FIG. 20 is a differential scanning calorimetry (DSC) profile of polymorphic Form VI of Compound I.

The DSC thermogram for Form VI, shown in FIG. 20, has an endotherm at 219.68° C., with two desolvation peaks at 88.42° C., 112° C. respectively.

G. Amorphous Form

The amorphous form can be prepared by lyophilization of aqueous solution of Compound I.

Figure 21:
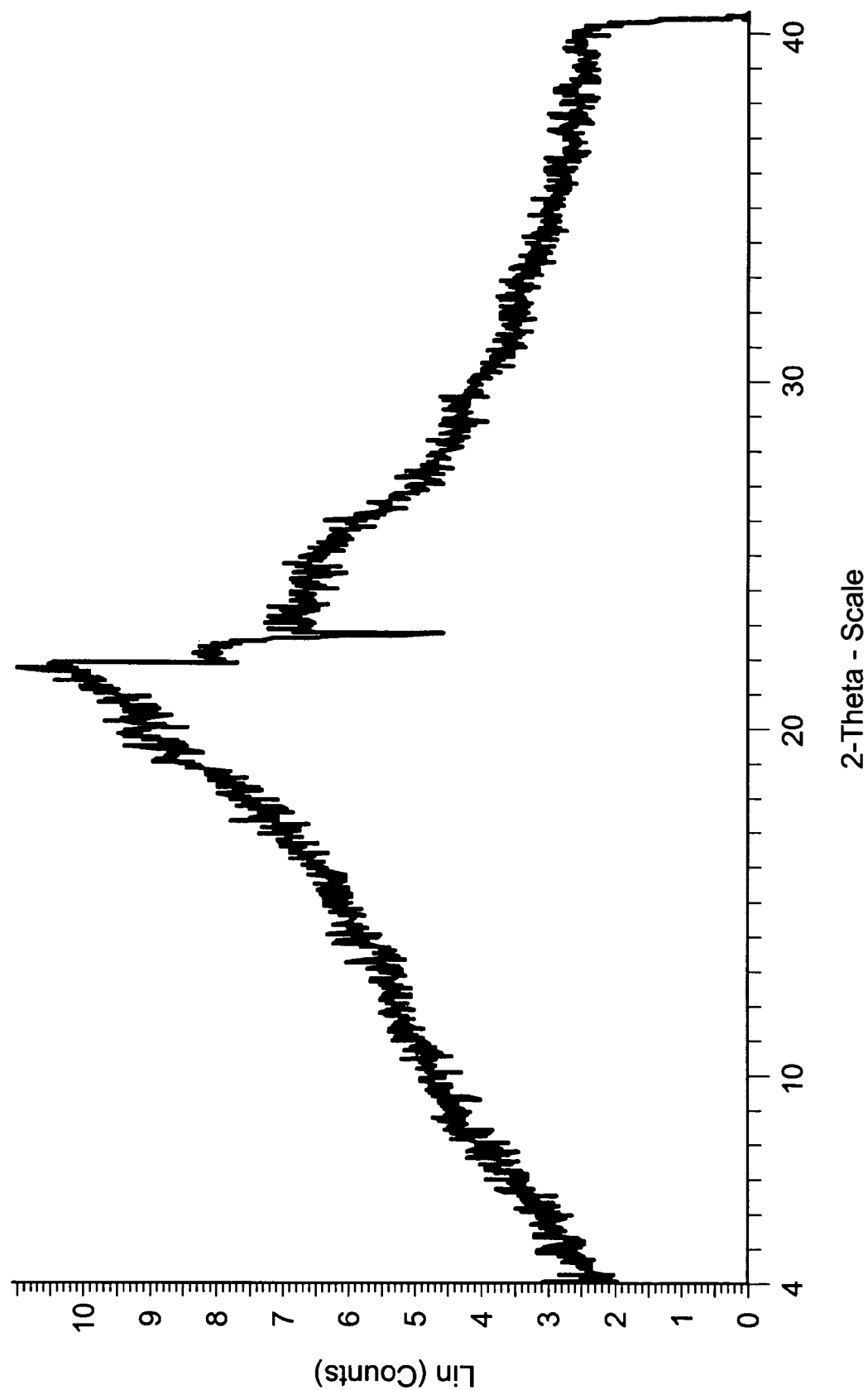
FIG. 21 is an X-ray powder diffraction diagram of an amorphous form of Compound I.

The X-ray powder diffraction pattern of the amorphous form is characterized by a typical amorphous broad hump-peak from 4 to 40°, without any sharp peaks characteristic of crystalline forms. FIG. 21 provides an X-ray powder diffraction pattern for the amorphous form.

Figure 22:
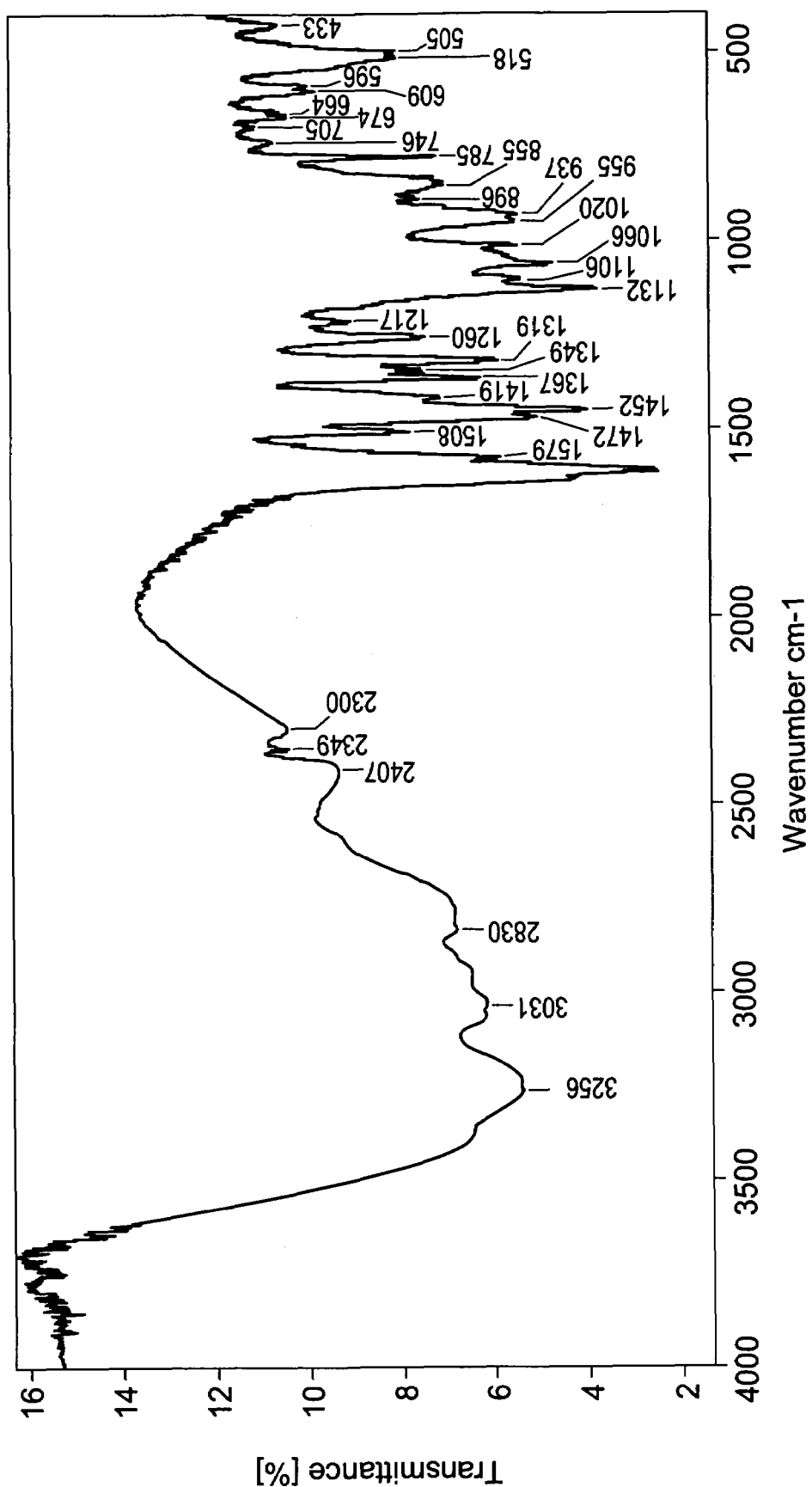
FIG. 22 is an infrared absorption spectrum of an amorphous form of Compound I.

The infrared absorption spectrum of amorphous form, shown in FIG. 22, was measured as described herein, with bands found at the flowing approximate positions (cm$^{-1}$): 433, 505, 518, 596, 609, 664, 674, 705, 746, 785, 856, 896, 937, 955, 1020, 1066, 1106, 1132, 1217, 1260, 1319, 1349, 1367, 1419, 1452, 1472, 1508, 1579, 2300, 2349, 2407, 2830, 3031, 3256.

Figure 23:
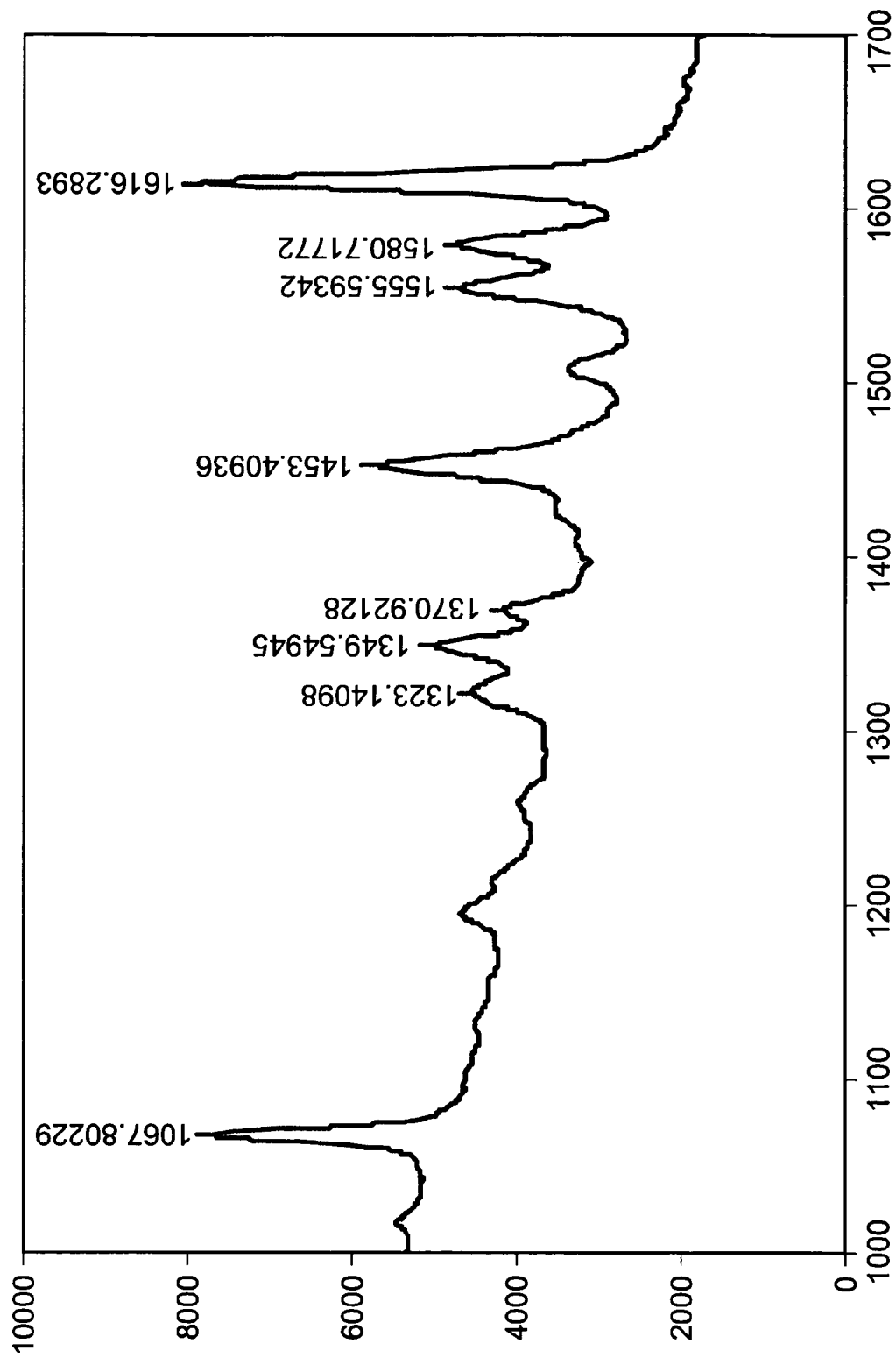
FIG. 23 is a Raman spectral diagram of an amorphous form of Compound I.

The Raman spectral diagram for the amorphous form, shown in FIG. 23, includes Raman Shift peaks (cm$^{-1}$) at approximately 1068, 1323, 1350, 1371, 1453, 1556, 1581, 1616.

Figure 24:
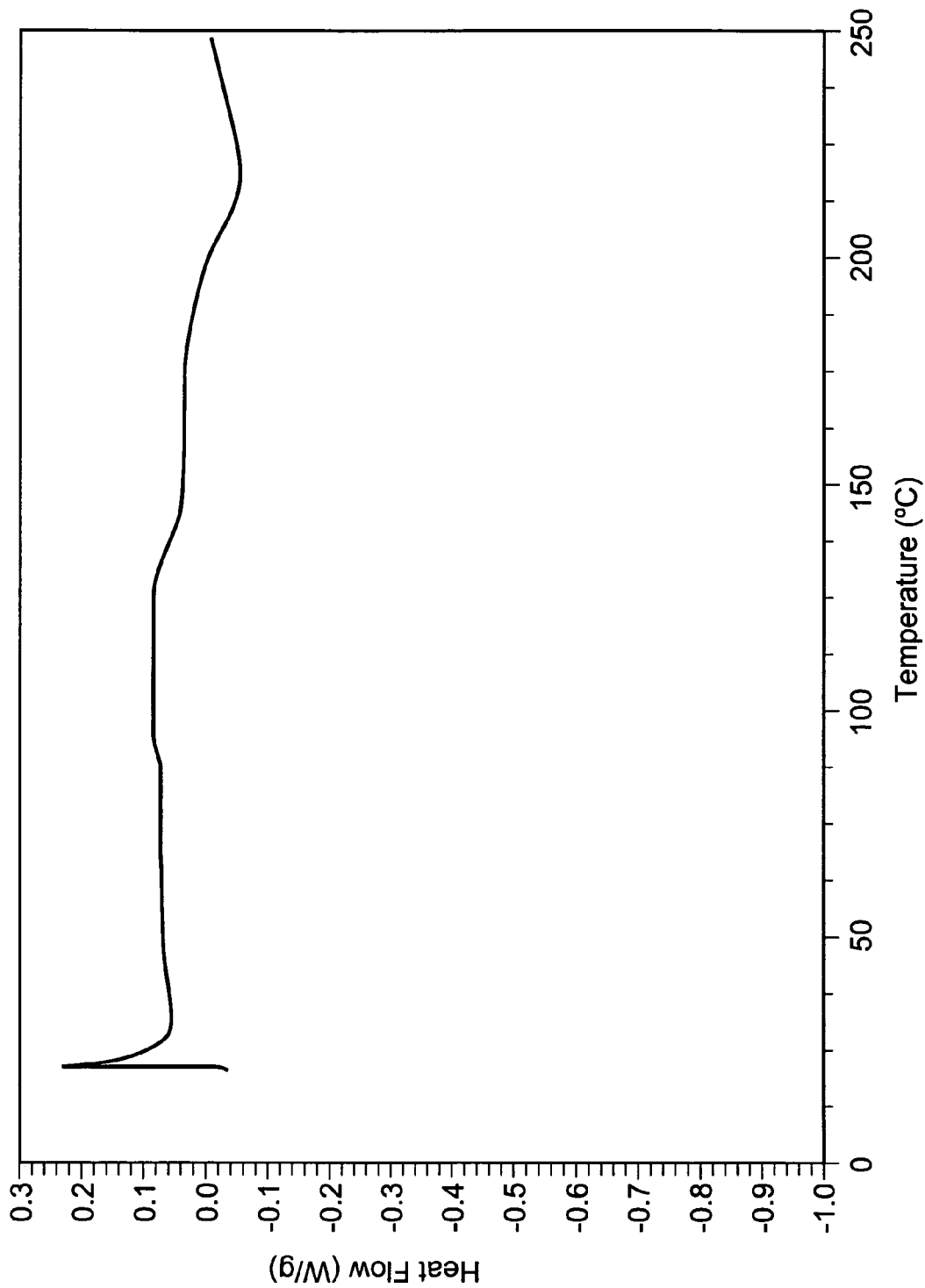
FIG. 24 is a differential scanning calorimetry (DSC) profile of an amorphous form of Compound I.

The DSC thermogram for the amorphous form, shown in FIG. 24, is notable for a lack of isolated peaks.

II. Pharmaceutical Compositions of the Invention

The active agents (i.e., the polymorphs, or solid forms comprising two or more such polymorphs or amorphous form, of Compound I described herein) of the invention may be formulated into pharmaceutical compositions suitable for mammalian medical use. Any suitable route of administration may be employed for providing a patient with an effective dosage of any of polymorphic Forms I, II, III, IV, V, VI, and amorphous form of Compound I. For example, peroral or parenteral formulations and the like may be employed. Dosage forms include capsules, tablets, dispersions, suspensions and the like, e.g. enteric-coated capsules and/or tablets, capsules and/or tablets containing enteric-coated pellets of Compound I. In all dosage forms, polymorphic Forms I, II, III, IV, V, VI, and amorphous form of Compound I can be admixtured with other suitable constituents. The compositions may be conveniently presented in unit dosage forms, and prepared by any methods known in the pharmaceutical arts. Pharmaceutical compositions of the invention comprise a therapeutically effective amount of the active agent and one or more inert, pharmaceutically acceptable carriers, and optionally any other therapeutic ingredients, stabilizers, or the like. The carrier(s) must be pharmaceutically acceptable in the sense of being compatible with the other ingredients of the formulation and not unduly deleterious to the recipient thereof. The compositions may further include diluents, buffers, binders, disintegrants, thickeners, lubricants, preservatives (including antioxidants), flavoring agents, taste-masking agents, inorganic salts (e.g., sodium chloride), antimicrobial agents (e.g., benzalkonium chloride), sweeteners, antistatic agents, surfactants (e.g., polysorbates such as "TWEEN 20" and "TWEEN 80", and pluronics such as F68 and F88, available from BASF), sorbitan esters, lipids (e.g., phospholipids such as lecithin and other phosphatidylcholines, phosphatidylethanolamines, fatty acids and fatty esters, steroids (e.g., cholesterol)), and chelating agents (e.g., EDTA, zinc and other such suitable cations). Other pharmaceutical excipients and/or additives suitable for use in the compositions according to the invention are listed in "Remington: The Science & Practice of Pharmacy", $19^{th}$ ed., Williams & Williams, (1995), and in the "Physician's Desk Reference", $52^{nd}$ ed., Medical Economics, Montvale, N.J. (1998), and in "Handbook of Pharmaceutical Excipients", Third Ed., Ed. A. H. Kibbe, Pharmaceutical Press, 2000. The active agents of the invention may be formulated in compositions including those suitable for oral, rectal, topical, nasal, ophthalmic, or parenteral (including intraperitoneal, intravenous, subcutaneous, or intramuscular injection) administration.

The amount of the active agent in the formulation will vary depending upon a variety of factors, including dosage form, the condition to be treated, target patient population, and other considerations, and will generally be readily determined by one skilled in the art. A therapeutically effective amount will be an amount necessary to modulate, regulate, or inhibit a PARP enzyme. In practice, this will vary widely depending upon the particular active agent, the severity of the condition to be treated, the patient population, the stability of the formulation, and the like. Compositions will generally contain anywhere from about 0.001% by weight to about 99% by weight active agent, preferably from about 0.01% to about 5% by weight active agent, and more preferably from about 0.01% to 2% by weight active agent, and will also depend upon the relative amounts of excipients/additives contained in the composition.

A pharmaceutical composition of the invention is administered in conventional dosage form prepared by combining a therapeutically effective amount of an active agent as an active ingredient with one or more appropriate pharmaceutical carriers according to conventional procedures. These procedures may involve mixing, granulating and compressing or dissolving the ingredients as appropriate to the desired preparation.

The pharmaceutical carrier(s) employed may be either solid or liquid. Exemplary solid carriers include sugars (for example, lactose, sucrose, mannitol, or sorbitol), talc, gelatin, agar, pectin, acacia, magnesium stearate, stearic acid and the like. Exemplary liquid carriers include syrup, peanut oil, olive oil, water and the like. Similarly, the carrier(s) may include time-delay or time-release materials known in the art, such as glyceryl monostearate or glyceryl distearate alone or with a wax, ethylcellulose, hydroxypropylmethylcellulose, methylmethacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation can be in the form of syrup, emulsion, soft gelatin capsule, sterile injectable solution or suspension in an ampoule or vial or non-aqueous liquid suspension.

To obtain a stable water-soluble dose form, Compound I can be dissolved in an aqueous solution of an organic or inorganic acid, such as 0.3 M solution of succinic acid or citric acid. If a soluble salt form is not available, the active agent may be dissolved in a suitable co-solvent or combinations of co-solvents. Examples of suitable co-solvents include, but are not limited to, alcohol, propylene glycol, polyethylene glycol 300, polysorbate 80, gylcerin and the like in concentrations ranging from 0-60% of the total volume. The composition may also be in the form of a solution of Compound I in an appropriate aqueous vehicle such as water or isotonic saline or dextrose solution.

It will be appreciated that the actual dosages of the active agents used in the compositions of this invention will vary according to the particular crystalline form being used, the particular composition formulated, the mode of administration and the particular site, host and disease being treated. Those skilled in the art using conventional dosage-determination tests in view of the experimental data for an agent can ascertain optimal dosages for a given set of conditions. For oral administration, an exemplary daily dose generally employed is from about 0.001 to about 1000 mg/kg of body weight, more preferably from about 0.001 to about 50 mg/kg body weight, with courses of treatment repeated at appropriate intervals. Administration of prodrugs is typically dosed at weight levels that are chemically equivalent to the weight levels of the fully active form. In the practice of the invention, the most suitable route of administration as well as the magnitude of a therapeutic dose will depend on the nature and severity of the disease to be treated. The dose, and dose frequency, may also vary according to the age, body weight, and response of the individual patient. In general, a suitable oral dosage form may cover a dose range from 5 mg to 250 mg total daily dose, administered in one single dose or equally divided doses. A preferred dosage range is from 10 mg to 80 mg. In general, a suitable parenteral dosage form may cover a dose range from 5 mg to 200 mg total daily dose, administered in one single dose or equally divided doses. A preferred dosage range is from 10 mg to 100 mg.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations that can be used pharmaceutically.

For oral administration, the compounds can be formulated readily by combining the active agents with pharmaceutically acceptable carriers known in the art. Such carriers enable the compounds of the invention to be formulated as tablets, pills, dragees, capsules, gels, syrups, slurries, suspensions and the like, for oral ingestion by a patient to be treated. Pharmaceutical preparations for oral use can be obtained using a solid excipient in admixture with the active agent, optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration intranasally or by inhalation, the compounds for use according to the present invention can be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The active agents may be formulated for parenteral administration by injection, e.g., by bolus injection or continuous infusion. Formulations for injection may be presented in unit-dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include suspensions of the active agents and may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active agents to allow for the preparation of highly concentrated solutions.

For administration to the eye, the active agent is delivered in a pharmaceutically acceptable ophthalmic vehicle such that the compound is maintained in contact with the ocular surface for a sufficient time period to allow the compound to penetrate the corneal and internal regions of the eye, including, for example, the anterior chamber, posterior chamber, vitreous body, aqueous humor, vitreous humor, cornea, iris/cilary, lens, choroid/retina and selera. The pharmaceutically acceptable ophthalmic vehicle may be, for example, an ointment, vegetable oil, or an encapsulating material. An active agent of the invention may also be injected directly into the vitreous and aqueous humor or subtenon.

Alternatively, the active ingredient may be in powder form for constitution with a suitable vehicle, e.g., sterile pyrogen-free water, before use. The compounds may also be formulated in rectal or vaginal compositions such as suppositories or retention enemas, e.g., containing conventional suppository bases such as cocoa butter or other glycerides.

In addition to the formulations described above, the polymorphic forms may also be formulated as a depot preparation. Such long-acting formulations may be administered by implantation (for example, subcutaneously or intramuscularly) or by intramuscular injection. Thus, for example, the polymorphic forms may be formulated with suitable polymeric or hydrophobic materials (for example, as an emulsion in an acceptable oil) or ion-exchange resins, or as sparingly soluble derivatives, for example, as a sparingly soluble salt.

Additionally, the active agents may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

III. Methods of Using the Polymorphs of the Invention

The inventive polymorphic forms of Compound I are useful for mediating the activity of poly(ADP-ribose) polymerase (PARP). More particularly, the polymorphic forms are useful as chemosensitizers that enhances the efficacy of radiotherapy or cytotoxic drugs whose mechanism depends on DNA damage. These drugs include but not limited to temozolomide (SCHERING), irinotecan (PFIZER), topotecan (GLAXO SMITHKLINE), cisplatin (BRISTOL MEYERS SQUIBB; AM PHARM PARTNERS; BEDFORD; GENSIA SICOR PHARMS; PHARMACHEMIE), and doxorubicin hydrochloride (AM PHARM PARTNERS; BEDFORD; GENSIA; SICOR PHARMS; PHARMACHEMIE; ADRIA; ALZA).

The inventive polymorphic forms of Compound I are also useful for enhancing the induction of the expression of Reg gene in β cells and HGF gene and, accordingly, promoting the proliferation of pancreatic β-cells of Langerhans' islets and suppressing apoptosis of the cells. Further, the inventive polymorphic forms of Compound I are useful for preparing cosmetics, for example, in after-sun lotions.

Therapeutically effective amounts of the agents of the invention may be administered, typically in the form of a pharmaceutical composition, to treat diseases mediated by modulation or regulation of PARP. An "effective amount" is intended to mean that amount of an agent that, when administered to a mammal, including a human, in need of such treatment, is sufficient to effect treatment for a disease mediated by the activity of one or more PARP enzyme. Thus, a therapeutically effective amount of a compound of the invention is a quantity sufficient to modulate, regulate, or inhibit the activity of one or more PARP enzyme such that a disease condition that is mediated by that activity is reduced or alleviated. The effective amount of a given compound will vary depending upon factors such as the disease condition and its severity and the identity and condition (e.g., weight) of the mammal in need of treatment, but can nevertheless be routinely determined by one skilled in the art. "Treating" is intended to mean at least the mitigation of a disease condition in a mammal, including a human, that is affected, at least in part, by the activity of one or more PARP enzymes and includes: preventing the disease condition from occurring in a mammal, particularly when the mammal is found to be predisposed to having the disease condition but has not yet been diagnosed as having it; modulating and/or inhibiting the disease condition; and/or alleviating the disease condition. Exemplary disease condition includes cancer.

The activity of the polymorphic forms of Compound I as modulators of PARP activity may be measured by any of the methods available to those skilled in the art, including in vivo and/or in vitro assays. Examples of suitable assays for activity measurements include those described in U.S. Pat. No. 6,495,541 and U.S. Provisional Patent Application No. 60/612,458, the disclosures of which are incorporated herein by reference in their entireties.

The present invention is also directed to therapeutic methods of treating a disease condition mediated by PARP activity, for example, cancer and a variety of disease and toxic states that involve oxidative or nitric oxide induced stress and subsequent PARP hyperactivation. Such conditions include, but not limited to, neurologic and neurodegenerative disorders (eg, Parkinson's disease, Alzheimer's disease), cardiovascular disorders (e.g., myocardial infarction, ischemia-reperfusion injury), diabetic vascular dysfunction, cisplatin-induced nephrotoxicity. The therapeutic methods of the present invention comprise administering to a mammal in need thereof a therapeutically effective amount of a pharmaceutical composition which comprises any of the polymorphic forms, or pharmaceutical compositions discussed above.

The present invention is also directed to combination therapeutic methods of treating a disease condition mediated by PARP activity, which comprises administering to a mammal in need thereof a therapeutically effective amount of a pharmaceutical composition which comprises any of the polymorphic forms, or pharmaceutical compositions discussed above, in combination with a therapeutically effective amount of one or more substances selected from anti-tumor agents, anti-angiogenesis agents, signal transduction inhibitors, and antiproliferative agents. Such substances include those disclosed in PCT Publication Nos. WO 00/38715, WO 00/38716, WO 00/38717, WO 00/38718, WO 00/38719, WO 00/38730, WO 00/38665, WO 00/37107 and WO 00/38786, the disclosures of which are incorporated herein by reference in their entireties.

Examples of anti-tumor agents include temozolomide (SCHERING), irinotecan (PFIZER), topotecan (GLAXO SMITHKLINE), cisplatin (BRISTOL MEYERS SQUIBB; AM PHARM PARTNERS; BEDFORD; GENSIA SICOR PHARMS; PHARMACHEMIE), and doxorubicin hydrochloride (AM PHARM PARTNERS; BEDFORD; GENSIA; SICOR PHARMS; PHARMACHEMIE; ADRIA; ALZA).

Additional examples of anti-tumor agents include mitotic inhibitors, for example vinca alkaloid derivatives such as vinblastine vinorelbine, vindescine and vincristine; colchines allochochine, halichondrine, N-benzoyltrimethylmethyl ether colchicinic acid, dolastatin 10, maystansine, rhizoxine, taxanes such as taxol (paclitaxel), docetaxel (Taxotere), 2'-N-[3-(dimethylamino)propyl]glutaramate (taxol derivative), thiocholchicine, trityl cysteine, teniposide, methotrexate, azathioprine, fluorouricil, cytocine arabinoside, 2'2'-difluorodeoxycytidine (gemcitabine), adriamycin and mitamycin. Alkylating agents, for example, carboplatin, oxiplatin, iproplatin, ethyl ester of N-acetyl-DL-sarcosyl-L-leucine (Asaley or Asalex), 1,4-cyclohexadiene-1,4-dicarbamic acid, 2,5-bis(1-azirdinyl)-3,6-dioxo-, diethyl ester (diaziquone), 1,4-bis(methanesulfonyloxy)butane (bisulfan or leucosulfan), chlorozotocin, clomesone, cyanomorpholinodoxorubicin, cyclodisone, dianhydroglactitol, fluorodopan, hepsulfam, mitomycin C, hycantheonemitomycin C, mitozolamide, 1-(2-chloroethyl)-4-(3-chloropropyl)-piperazine dihydrochloride, piperazinedione, pipobroman, porfiromycin, spirohydantoin mustard, teroxirone, tetraplatin, thiotepa, triethylenemelamine, uracil nitrogen mustard, bis(3-mesyloxypropyl)amine hydrochloride, mitomycin, nitrosoureas agents such as cyclohexylchloroethylnitrosourea, methylcyclohexyl-chloroethylnitrosourea, 1-(2-chloroethyl)-3-(2,6-dioxo-3-piperidyl)-1-nitroso-urea, bis(2-chloroethyl)nitrosourea, procarbazine, dacarbazine, nitrogen mustard-related compounds such as mechloroethamine, cyclophosphamide, ifosamide, melphalan, chlorambucil, estramustine sodium phosphate, and strptozoin. DNA anti-metabolites, for example 5-fluorouracil, cytosine arabinoside, hydroxyurea, 2-[(3-hydroxy-2-pyrinodinyl)methylene]-hydrazinecarbothioamide, deoxyfluorouridine, 5-hydroxy-2-formylpyridine thiosemicarbazone, alpha-2'-deoxy-6-thioguanosine, aphidicolin glycinate, 5-azadeoxycytidine, beta-thioguanine deoxyriboside, cyclocytidine, guanazole, inosine glycodialdehyde, macbecin II, pyrazolimidazole, cladribine, pentostatin, thioguanine, mercaptopurine, bleomycin, 2-chlorodeoxyadenosine, inhibitors of thymidylate synthase such as raltitrexed and pemetrexed disodium, clofarabine, floxuridine and fludarabine. DNA/RNA antimetabolites, for example, L-alanosine, 5-azacytidine, acivicin, aminopterin and derivatives thereof such as N-[2-chloro-5-[[[(2,4-diamino-5-methyl-6-quinazolinyl)methyl]amino]benzoyl]-L-aspartic acid, N-[4-[[(2,4-diamino-5-ethyl-6-quinazolinyl) methyl]amino]benzoyl]-L-aspartic acid, N-[2-chloro-4-[[(2, 4-diaminopteridinyl)methyl]amino]benzoyl]-L-aspartic acid, soluble Baker's antifol, dichloroallyl lawsone, brequinar, ftoraf, dihydro-5-azacytidine, methotrexate, N-(phosphonoacetyl)-L-aspartic acid tetrasodium salt, pyrazofuran, trimetrexate, plicamycin, actinomycin D, cryptophycin, and analogs such as cryptophycin-52 or, for example, one of the preferred anti-metabolites disclosed in European Patent Application No. 239362 such as $\underline{N}$-(5-[$\underline{N}$-(3,4-dihydro-2-methyl-4-oxoquinazolin-6-ylmethyl)-$\underline{N}$-methylamino]-2-thenoyl)-L-glutamic acid; growth factor inhibitors; cell cycle inhibitors; intercalating antibiotics, for example adriamycin and bleomycin; proteins, for example interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of the treatment.

Anti-angiogenesis agents include MMP-2 (matrix-metalloprotienase 2) inhibitors, MMP-9 (matrix-metalloprotienase 9) inhibitors, and COX-II (cyclooxygenase II) inhibitors. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are herein incorporated by reference in their entirety. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Examples of MMP inhibitors include AG-3340, RO 32-3555, RS 13-0830, and the following compounds: 3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo [3.2.1]octane-3-carboxylic acid hydroxyamide; (2R, 3R) 1-[4-(2-chloro-4-fluoro-benzyloxy)-benzenesulfonyl]-3-hydroxy-3-methyl-piperidine-2-carboxylic acid hydroxamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; 3-[4-(4-chloro-phenoxy)-benzenesulfonylamino]-tetrahydro-pyran-3-carboxylic acid hydroxyamide; (2R, 3R) 1-[4-(4-fluoro-2methyl-benzyloxy)-benzenesulfonyl]-3-hydroxy-3-methyl-piperidine-2-carboxylic acid hydroxyamide; 3-[[4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxa-bicyclo[3.2.1] octane-3-carboxylic acid hydroxyamide; 3-endo-3-[4-(4-fluoro-phenoxy)-benzenesulfonylamino]-8-oxa-bicyclo [3.2.1]octane-3-carboxylic acid hydroxyamide; 3-[4-(4-fluoro-phenoxy)-benzenesulfonylamino]-tetrahydro-furan-3-carboxylic acid hydroxyamide; and pharmaceutically acceptable salts, solvates and hydrates thereof.

Examples of signal transduction inhibitors include agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, for example, HERCEPTIN™ (Genentech, Inc. of South San Francisco, Calif., USA).

EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998). EGFR-inhibiting agents include, but are not limited to, the monoclonal antibodies C225 and anti-EGFR 22Mab (ImClone Systems Incorporated of New York, N.Y., USA), the compounds ZD-1839 (AstraZeneca), BIBX-1382 (Boehringer Ingelheim), MDX-447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Mass.).

VEGF inhibitors, for example SU-5416 and SU-6668 (Sugen Inc. of South San Francisco, Calif., USA), can also be combined or co-administered with the composition. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are herein incorporated by reference in their entirety. Other examples of some specific VEGF inhibitors are IM862 (Cytran Inc. of Kirkland, Wash., USA); anti-VEGF monoclonal antibody bevacizumab (Genentech, Inc. of South San Francisco, Calif.); and angiozyme, a synthetic ribozyme from Ribozyme (Boulder, Colo.) and Chiron (Emeryville, Calif.).

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), may be administered in combination with the composition. Such erbB2 inhibitors include those described in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), each of which is herein incorporated by reference in its entirety. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are herein incorporated by reference in their entirety.

Other antiproliferative agents that may be used include inhibitors of the enzyme farnesyl protein transferase and inhibitors of the receptor tyrosine kinase PDGFr, including the compounds disclosed and claimed in the following U.S. patent application Ser. Nos.: 09/221,946 (filed Dec. 28, 1998); 09/454,058 (filed Dec. 2, 1999); 09/501,163 (filed Feb. 9, 2000); 09/539,930 (filed Mar. 31, 2000); 09/202,796 (filed May 22, 1997); 09/384,339 (filed Aug. 26, 1999); and Ser. No. 09/383,755 (filed Aug. 26, 1999); and the compounds disclosed and claimed in the following U.S. provisional patent application Nos.: 60/168,207 (filed Nov. 30, 1999); 60/170,119 (filed Dec. 10, 1999); 60/177,718 (filed Jan. 21, 2000); 60/168,217 (filed Nov. 30, 1999), and 60/200,834 (filed May 1, 2000). Each of the foregoing patent applications and provisional patent applications is herein incorporated by reference in their entirety.

Compositions of the invention can also be used with other agents useful in treating abnormal cell growth or cancer, including, but not limited to, agents capable of enhancing antitumor immune responses, such as CTLA4 (cytotoxic lymphocite antigen 4) antibodies, and other agents capable of blocking CTLA4; and anti-proliferative agents such as other farnesyl protein transferase inhibitors. Specific CTLA4 antibodies that can be used in the present invention include those described in U.S. Provisional Application No. 60/113,647 (filed Dec. 23, 1998), which is herein incorporated by reference in its entirety.

The disclosures of all cited references are incorporated herein by reference in their entirety.

EXAMPLES

The examples which follow will further illustrate the preparation of the distinct polymorphic forms of the invention, i.e., polymorphic Forms I, II, III, IV, V, VI, and amorphous form of Compound I, but are not intended to limit the scope of the invention as defined herein or as claimed below. Unless otherwise indicated, all temperatures are set forth in degrees Celsius and all parts and percentages are by weight.

Example 1

Preparation and Characterization of Polymorphic Form IV (Methanol Solvate) of Compound I Polymorphic Form IV of Compound I was prepared by the following procedure. A 500 mL round bottom flask was charged with the compound 8-fluoro-2-{4-[(methylamino)methyl]phenyl}-1,3,4,5-tetrahydro-6H-azepino[5,4,3-cd]indol-6-one represented by formula 1 (1.65 g, 5.10 mmol, 1.0 equiv.) and methanol (200 mL). The mixture was agitated until clear solution was obtained (~10 minutes). A 0.5 M phosphoric acid solution in methanol (11.0 mL, 5.87 mmol, 1.15 equiv., prepared by dissolving 0.7 g of 85% phosphoric acid in 11.0 mL of methanol) was added. The resulting mixture was stirred for at 30 minutes at ambient temperature. The solids obtained were filtered and dried at 45° C. to afford polymorphic Form IV of the phosphate salt of 8-fluoro-2-{4-[(methylamino)methyl]phenyl}-1,3,4,5-tetrahydro-6H-azepino[5,4,3-cd]indol-6-one (1.43 g).

FIG. 10 is an X-ray powder diffractogram of polymorphic Form IV of Compound I. FIG. 11 is an infrared absorption spectrum of polymorphic Form IV. Polymorphic Form IV of Compound I was further characterized by differential scanning calorimetry (FIG. 12).

Example 2

Preparation and Characterization of Polymorphic Form I (Hydrate A) of Compound I Polymorphic Form I of Compound I was produced by the following procedure. A 50 mL round bottom flask was charged with polymorphic Form IV (methanol solvate) of Compound I (1.0 g) slurried with 10 mL of water and stirred for at 18-24 hrs at ambient temperature. The solids obtained were filtered, dried at 45° C. to afford polymorphic Form I of Compound I (0.67 g). The product was analyzed for absence of methanol by NMR.

FIG. 1 is an X-ray powder diffractogram of polymorphic Form I of Compound I. FIG. 2 is an infrared absorption spectrum of polymorphic Form I. Polymorphic Form I of Compound I was further characterized by differential scanning calorimetry (FIG. 3).

Example 3

Preparation and Characterization of Polymorphic Form II (Anhydrous Form) of Compound I Form II was produced:
(a) by heating Form I at 60° C. overnight;
(b) by keeping Form I under vacuum at room temperature overnight; or
(c) by keeping Form I at 25° C. under 0% relative humidity over 5 hours.

FIG. 4 is an X-ray powder diffractogram of polymorphic Form II of Compound I. FIG. 5 is an infrared absorption spectrum of polymorphic Form II. Polymorphic Form II of Compound I was further characterized by differential scanning calorimetry (FIG. 6).

Form II is stored at 2-8° C. with desiccant.

Example 4

Preparation and Characterization of Polymorphic Form III (Hydrate B) of Compound I Polymorphic Form III of Compound I was prepared:
(a) by exposing Form I to 90% relative humidity at 25° C. over 5 hours;
(b) by exposing Form I to 75% relative humidity at 40° C. for 1 week; or
(c) by exposing Form II to 75% relative humidity at 40° C. overnight.

FIG. 7 is an X-ray powder diffractogram of polymorphic Form III of Compound I. FIG. 8 is an infrared absorption spectrum of polymorphic Form III. Polymorphic Form III of Compound I was further characterized by differential scanning calorimetry (FIG. 9).

Example 5

Preparation and Characterization of Polymorphic Form V (Hydrate C) of Compound I Polymorphic Form V of Compound I was formed during the stability studies of Form II when stored at 40° C. under 75% relative humidity for 6 months period. Polymorphic Form V of Compound I is physically and chemically stable at room temperature for at least 3 months.

Polymorphic Form V of Compound I has an aqueous solubility of 3.0 mg/mL at pH 5.4.

FIG. 13 provides an X-ray powder diffraction pattern of Form V. FIG. 16 is an infrared absorption spectrum of polymorphic Form V of Compound I. The DSC thermogram for Form V has an endotherm at 199.40° C., with two desolvation peaks at 57.29° C. and 110.73° C., respectively (FIG. 17).

Example 6

Preparation and Characterization of Polymorphic Form VI of Compound I

Polymorphic Form VI of Compound I can be prepared by taking an aqueous slurry of Form II and heating at 100° C. overnight. As shown in FIG. 14, conversion began at 80° C. and was complete following the overnight hold at 100° C.

Polymorphic Form VI has the characteristics described above. FIG. 18 is an X-ray powder diffraction diagram of polymorphic Form VI of Compound I. FIG. 19 is an infrared absorption spectrum of polymorphic Form VI of Compound I. FIG. 20 is a differential scanning calorimetry (DSC) profile of polymorphic Form VI of Compound I.

Example 7

Use of Polymorphic Form II (Anhydrous Form) of Compound I for Preparation of Pharmaceutical Composition A. Complete Composition Polymorphic Form II (Anhydrous Form) of Compound I was used for preparation of a lyophilized powder for injection, 12 mg/vial (as free base), intended for clinical use, are provided below.

The drug product is first formulated as a Compound I solution for lyophilization. The quantitative composition of the Compound I solution for lyophilization is presented in Table 2.

TABLE 2

Compound I Solution for Lyophilization, 3 mg/mL (as free base)

| Names of Ingredients | Theoretical Quantity (mg/mL) | Percentage Formula (% w/w) | Function |
|---|---|---|---|
| Compound I | 3.9 (Equivalent to 3.0 of its free base) | 0.4 | Active ingredient |
| Mannitol | 50.0 | 4.9 | Bulking agent |

TABLE 2-continued

Compound I Solution for Lyophilization, 3 mg/mL (as free base)

| Names of Ingredients | Theoretical Quantity (mg/mL) | Percentage Formula (% w/w) | Function |
|---|---|---|---|
| Water for Injection | 963.1 | 94.7 | Solvent |
| Total | 1017.0 | 100.0 | — |

The quantitative unit composition of Compound I lyophilized powder for injection is presented in

TABLE 3

Lyophilized Powder for Injection, 12 mg/vial (as free base)

| Names of Ingredients | Theoretical Quantity (mg/Vial) | Percentage Formula (% w/w) | Function |
|---|---|---|---|
| Compound I | 16.17 (Equivalent to 12.45 of its free base) | 7.2 | Active ingredient |
| Mannitol | 207.50 | 92.8 | Bulking agent |
| Water for Injection | Trace | Trace | Solvent |
| Nitrogen | Trace | Trace | Vial headspace |
| Total | 223.67 | 100.0 | — |

B. Overage

The clinical composition of Compound I Lyophilized Powder for Injection, 12 mg/vial (as free base), contains a theoretical overage of 0.45 mg/vial (as free base). This overage compensates for the solid volume in the vial upon reconstitution with 6 mL of Sterile Water for Injection (SWFI) and ensures the delivery of a 2.02 mg/mL (as free base) drug solution.

C. Container

The components of the packaging system for Compound I Lyophilized Powder for Injection, 12 mg/vial (as free base), are listed below:

| Component | Description |
|---|---|
| Vial | 10 mL/20 mm, Type I amber glass vial |
| Stopper | 20 mm 4432/50 (uncoated chlorobutyl) B2-40 stopper, 1319 design |
| Seal | 20 mm aluminum overcap |

D. Development Pharmaceutics and Rationale for Choice of Dosage Form

Lyophilized Powder for Injection is a conventional dosage form for administration. The clinical formulation contains mannitol as a bulking agent and a tonicity adjuster. Reconstitution of the drug product with 6 mL SWFI yields a clear, hypotonic, 2.02 mg/mL (as free base) solution. The reconstituted drug product will be diluted with an acceptable isotonic sterile diluent for infusion.

The clinical drug product was originally designed for reconstitution with 4 mL SWFI to yield a clear, isotonic, 3 mg/mL (as free base) solution. During drug product stability evaluation, incidents of haziness/turbidity in the constituted solution were observed and investigated. The haziness/turbidity was attributed to drug crystallization of a drug substance polymorph (Hydrate B). The aqueous solubility of polymorphic Form III (Hydrate B) is 2.7 mg/mL at pH 5.4 and is thus very close to the original target drug product reconstitution concentration (3 mg/mL). The SWFI reconstitution volume was changed from 4 mL to 6 mL to ensure complete drug dissolution. The resulting final concentration of the constituted drug product solution is 2.02 mg/mL (as free base), well below the aqueous solubility of polymorphic Form III (Hydrate B).

E. Clinical Manufacturing Formula, Manufacturing Process, In-Process Controls and Assembly Process The manufacturing process for Compound I Lyophilized Powder for Injection, 12 mg/vial (as free base) is summarized below. The current clinical batch size is 9.3 L per manufacturing campaign. The manufacturing formula is the same as the clinical composition (see Table 2 and Table 3).

a) Add approximately 75% of the total amount of Water for Injection (WFI) into the compounding vessel.

b) Add and completely dissolve the required quantity of mannitol in WFI with mixing.

c) Warm the WFI/mannitol solution to approximately 58° C., add the required quantity of Compound I drug substance, and mix until completely dissolved.

d) Bring the solution to final volume by weight with WFI, mix for 10 minutes, and cool the solution to room temperature.

e) Sample aliquots for in-process control testing (i.e., appearance, pH, density, and UV assay).

f) Sterile filter the bulk solution for lyophilization through 0.45 μm and 0.22 μm membrane filters and fill 4.15 mL (includes a 0.15 mL overfill) into 10 mL/20 mm, Type I amber glass vials under aseptic conditions.

g) Lyophilize the filled vials with partially inserted stoppers.

h) At the end of the lyophilization cycle, back fill with nitrogen and stopper the vials under slight vacuum at room temperature.

i) Seal the lyophilized vials with aluminum overcaps.

j) Place vials into refrigerated storage.

Example 8

Preparation and Characterization of Amorphous Form of Compound I

The amorphous form of Compound I was prepared by dissolving polymorphic Form II (anhydrous form) of Compound I in sterile water for injection at concentration of 4.46 mg/mL. 2 mL of this solution was filled in 10 mL clear Type I vial and lyophilized in FTS LyoStar Lyophilizer (S/N LSACC3). The lyophilization cycle is described as follows.

The product was frozen to −50° C. and subsequently vacuum dried at −30° C., −20° C. and −15° C. for 12 hr each to complete the primary drying step. The vacuum pressure was kept at 200 mtorr. The product was further dried at 25° C. and at vacuum 200 mtorr for 24 hr to complete the secondary drying step.

The amorphous form of Compound I was obtained as the white/yellowish lyophilized cake. The amorphous form of Compound I can be reconstituted with 2 mL sterile water for injection to yield a clear yellow solution.

We claim:

1. A crystalline phosphate salt of 8-fluoro-2-{4-[(methylamino)methyl]phenyl}1,3,4,5-tetrahydro-6H-azepino[5,4,3-cd]indol-6-one, wherein the crystalline phosphate salt is selected from the group consisting of polymorph Form I, Form II, Form III, Form V, and Form VI.

2. The crystalline phosphate salt of claim 1, wherein the crystalline phosphate salt is a substantially pure polymorph of Form II.

3. The crystalline phosphate salt of claim 1, wherein the crystalline phosphate salt has a X-ray powder diffraction pattern comprising peaks at diffraction angles (2θ) of 11.2, 14.0, 20.1, and 23.1.

4. The crystalline phosphate salt of claim 1, wherein the crystalline phosphate salt has a X-ray powder diffraction pattern comprising peaks at diffraction angles (2θ) essentially the same as shown in FIG. 4.

5. A phosphate salt of 8-fluoro-2-{4-[(methylamino)methyl]phenyl}1,3,4,5-tetrahydro-6H-azepino[5,4,3-cd]indol-6-one, wherein the salt is a substantially pure amorphous form.

6. A solid form of a phosphate salt of 8-fluoro-2-{4-[(methylamino)methyl]phenyl}-1,3,4,5-tetrahydro-6H-azepino[5,4,3-cd]indol-6-one, wherein the solid form comprises at least two of the following forms: polymorph Forms I, II, III, V, VI, or an amorphous form.

* * * * *